United States Patent
Dumont et al.

(10) Patent No.: US 9,880,052 B2
(45) Date of Patent: Jan. 30, 2018

(54) METHODS, SYSTEMS, AND APPARATUSES FOR ACCURATE MEASUREMENT AND REAL-TIME FEEDBACK OF SOLAR ULTRAVIOLET EXPOSURE

(71) Applicant: THE JOAN AND IRWIN JACOBS TECHNION-CORNELL INNOVATION INSTITUTE, New York, NY (US)

(72) Inventors: Emmanuel Dumont, New York, NY (US); Shayak Banerjee, Hartsdale, NY (US); Mauricio Contreras, Santiago (CL)

(73) Assignee: The Joan and Irwin Jacobs Technion-Cornell Innovation Institute, New York, NY (US)

( * ) Notice: Subject to any disclaimer, the term of this patent is extended or adjusted under 35 U.S.C. 154(b) by 0 days.

(21) Appl. No.: 15/247,837

(22) Filed: Aug. 25, 2016

(65) Prior Publication Data

US 2016/0363479 A1    Dec. 15, 2016

Related U.S. Application Data

(60) Provisional application No. 62/209,813, filed on Aug. 25, 2015, provisional application No. 62/233,173, (Continued)

(51) Int. Cl.
*G01J 1/42* (2006.01)
*G01B 11/14* (2006.01)
(Continued)

(52) U.S. Cl.
CPC .............. *G01J 1/4204* (2013.01); *G01B 11/14* (2013.01); *G01J 1/0271* (2013.01); *G01J 1/0403* (2013.01);
(Continued)

(58) Field of Classification Search
CPC .............................. G01J 1/4204; G01J 1/4228
(Continued)

(56) References Cited

U.S. PATENT DOCUMENTS 376,547 A    1/1888   Pratt
2,949,880 A  8/1960   Stephen
(Continued)

FOREIGN PATENT DOCUMENTS

JP    2011-221010 A    11/2011
WO    WO01/52736 A1    7/2001
(Continued)

OTHER PUBLICATIONS

Microsoft; Microsoft Band Official Sife "Live healthier and be more productive"; Ad; Microsoft; retrieved on Dec. 9, 2014 from http://www.microsoft.com/microsoft-band/en-us; 22 pages.*
(Continued)

*Primary Examiner* — David Porta
*Assistant Examiner* — Abra Fein
(74) *Attorney, Agent, or Firm* — Shay Glenn LLP

(57) ABSTRACT

Systems and methods for accurate measurement and real-time feedback of solar ultraviolet exposure for management of ultraviolet dose. The systems can include a wearable device including a proximity sensor, the proximity sensor used to initiate an alert that the proximity sensor is covered. The systems can include a visible light sensor, the visible light sensor used to enter into a sleep, or night, mode.

6 Claims, 19 Drawing Sheets

Related U.S. Application Data filed on Sep. 25, 2015, provisional application No. 62/233,190, filed on Sep. 25, 2015.

(51) Int. Cl.
| | | |
|---|---|---|
| *G06F 1/32* | (2006.01) | |
| *G01J 1/02* | (2006.01) | |
| *G01J 1/04* | (2006.01) | |
| G06F 19/00 | (2011.01) | |
| G08B 21/02 | (2006.01) | |

(52) U.S. Cl.
CPC ............ *G01J 1/429* (2013.01); *G06F 1/3287* (2013.01); *G01J 2001/4266* (2013.01); *G06F 19/363* (2013.01); *G08B 21/02* (2013.01)

(58) Field of Classification Search
USPC ........................................................ 250/372
See application file for complete search history.

(56) References Cited

U.S. PATENT DOCUMENTS

| | | | |
|---|---|---|---|
| 3,268,839 | A | 8/1966 | McFarland |
| 3,878,496 | A | 4/1975 | Erickson |
| 4,229,733 | A | 10/1980 | Tulenko et al. |
| 4,255,665 | A | 3/1981 | Shriner |
| 4,348,664 | A | 9/1982 | Boschetti et al. |
| 4,428,050 | A | 1/1984 | Pellegrino et al. |
| 4,726,688 | A | 2/1988 | Ruel |
| 4,851,686 | A | 7/1989 | Pearson |
| 5,008,548 | A | 4/1991 | Gat |
| 5,036,311 | A | 7/1991 | Moran et al. |
| 5,148,023 | A | 9/1992 | Hayashi et al. |
| 5,151,600 | A | 9/1992 | Black |
| 5,204,532 | A | 4/1993 | Rosenthal |
| 5,365,068 | A | 11/1994 | Dickerson |
| 5,382,799 | A | 1/1995 | May |
| 5,497,004 | A | 3/1996 | Rudolph et al. |
| 5,500,532 | A | 3/1996 | Kozicki |
| 5,731,589 | A | 3/1998 | Sief et al. |
| 5,992,996 | A | 11/1999 | Sawyer |
| 6,201,250 | B1 | 3/2001 | Morlock |
| 6,322,503 | B1 | 11/2001 | Sparhawk |
| 6,426,503 | B1 | 7/2002 | Wüest |
| 6,437,346 | B1 | 8/2002 | Goudjil |
| 6,439,763 | B2 | 8/2002 | Roeder et al. |
| 6,582,380 | B2 | 6/2003 | Kazlausky et al. |
| D479,805 | S | 9/2003 | Tsai |
| 6,729,756 | B2 | 5/2004 | Sezai |
| 6,967,447 | B2 | 11/2005 | Lim et al. |
| 7,148,489 | B2 | 12/2006 | Yagi |
| 7,227,153 | B2 | 6/2007 | Yagi |
| 7,230,222 | B2 | 6/2007 | Cheng et al. |
| 7,265,358 | B2 | 9/2007 | Fontaine |
| 7,500,746 | B1 | 3/2009 | Howell et al. |
| 7,635,906 | B2 | 12/2009 | Nakamura et al. |
| 7,709,812 | B2 | 5/2010 | Simon et al. |
| 7,874,666 | B2 | 1/2011 | Xu et al. |
| 8,044,363 | B2 | 10/2011 | Ales et al. |
| 8,109,629 | B2 | 2/2012 | Howell et al. |
| 8,157,730 | B2 | 4/2012 | LeBoeuf et al. |
| 8,434,863 | B2 | 5/2013 | Howell et al. |
| 8,487,267 | B2 | 7/2013 | Abe et al. |
| 8,558,155 | B2 | 10/2013 | Tomlinson et al. |
| 8,586,938 | B2 | 11/2013 | Tsubata et al. |
| 8,605,802 | B2 | 12/2013 | Lee et al. |
| 8,829,457 | B2 | 9/2014 | Smith et al. |
| 9,068,887 | B1 | 6/2015 | Bennouri et al. |
| 9,360,364 | B2 | 6/2016 | Hingorani et al. |
| 9,368,537 | B1 | 6/2016 | Holmes et al. |
| 2003/0150998 | A1 | 8/2003 | Shin et al. |
| 2004/0149921 | A1 | 8/2004 | Smyk |
| 2004/0225530 | A1 | 11/2004 | Bell et al. |
| 2005/0190655 | A1 | 9/2005 | Blumberg |
| 2005/0226446 | A1* | 10/2005 | Luo ......... H04R 25/00 381/312 |
| 2006/0289779 | A1 | 12/2006 | Marmaropoulos |
| 2007/0073487 | A1 | 3/2007 | Albright et al. |
| 2007/0170366 | A1 | 7/2007 | Lin et al. |
| 2008/0103561 | A1 | 5/2008 | Moscovici |
| 2008/0217611 | A1 | 9/2008 | Nakamura et al. |
| 2009/0090865 | A1 | 4/2009 | Lub et al. |
| 2009/0296533 | A1 | 12/2009 | Kojima |
| 2010/0163750 | A1 | 7/2010 | Hunwick, III et al. |
| 2010/0308105 | A1* | 12/2010 | Savarese ......... A63B 57/00 235/375 |
| 2011/0133103 | A1 | 6/2011 | Folkesson |
| 2011/0190595 | A1* | 8/2011 | Bennett ......... A61B 1/00016 600/301 |
| 2011/0191272 | A1 | 8/2011 | McGuire |
| 2012/0115512 | A1 | 5/2012 | Grainger et al. |
| 2012/0241618 | A1* | 9/2012 | Hsu ............ H01L 27/1462 250/338.1 |
| 2012/0326046 | A1* | 12/2012 | Aslam ............ G01J 1/0233 250/372 |
| 2013/0020477 | A1 | 1/2013 | Castellan et al. |
| 2013/0096466 | A1 | 4/2013 | Sarrafzadeh et al. |
| 2014/0032165 | A1 | 1/2014 | Sarrafzadeh et al. |
| 2014/0092238 | A1* | 4/2014 | Sandhu ........... G01J 1/429 348/135 |
| 2014/0145860 | A1 | 5/2014 | Park et al. |
| 2014/0296658 | A1* | 10/2014 | Yuen .......... A61B 5/6885 600/301 |
| 2014/0374600 | A1 | 12/2014 | Gokingco et al. |
| 2015/0041663 | A1 | 2/2015 | Oliver et al. |
| 2015/0102208 | A1 | 4/2015 | Appelboom et al. |
| 2015/0136975 | A1* | 5/2015 | Sugaya ......... H01J 49/0422 250/288 |
| 2015/0168365 | A1 | 6/2015 | Conner |
| 2015/0177055 | A1 | 6/2015 | Lian et al. |
| 2015/0177059 | A1 | 6/2015 | Lian et al. |
| 2015/0177063 | A1 | 6/2015 | Lian et al. |
| 2015/0294080 | A1 | 10/2015 | Garnavi et al. |
| 2015/0346025 | A1 | 12/2015 | Spinella et al. |
| 2015/0347625 | A1 | 12/2015 | Werneck et al. |
| 2016/0109959 | A1* | 4/2016 | Heo ............ G06F 3/015 340/5.52 |

FOREIGN PATENT DOCUMENTS

| | | | | |
|---|---|---|---|---|
| WO | WO2005/103923 | A2 | 11/2005 | |
| WO | WO2011/094742 | A2 | 8/2011 | |
| WO | WO2013/034288 | A1 | 3/2013 | |
| WO | WO 2013034288 | A1 * | 3/2013 | ............ G01J 1/429 |
| WO | WO2013/106653 | A1 | 7/2013 | |

OTHER PUBLICATIONS

Amini et al.; A wireless embedded device for personalized ultraviolet monitoring; Biodevices; 9; pp. 200-205; 2009.

Bharatula et al.; Towards wearable autonomous microsystems; Pervasive Computing: Proceedings of the 2nd Int'l Conference; pp. 225-237; Vienna, Austria; Apr. 18-23, 2004.

CDC; Sunburn prevalence among adults—United States 1991, 2003 and 2004; MMWR Weekly; 56(21); pp. 524-528; (9 pgs. printed); Jun. 1, 2007.

Chang et al.; Sun exposure and melanoma risk at different latitudes: a pooled analysis of 5700 cases and 7216 controls; Int J Epidemiol.; 38(3); pp. 814-830; Jun. 2009.

Chiche et al.; Seasonal variations of systemic lupus erythematosus flares in southern France; Eur. J. Intern. Med.; 23(3); pp. 250-254; Apr. 2012.

Corral et al; Bright light therapy's effect on postrpartum depression; Am J Psychiatry; 157(2); pp. 303-304; Feb. 2000.

Corrêa et al.; Comparison between UV index measurements performed by research-grade and consumer-products instrucments; Photochem. Photobiol. Sci.; 9; pp. 459-463; online: Mar. 19, 2010.

Cortes et al.; Support-vector networks; Machine Learning; 20(3); pp. 273-297; Sep. 1995.

(56) References Cited

OTHER PUBLICATIONS

Dennis et al.; Sunburns and risk of cutaneous melanoma: does age matter? A comprehensive meta-analysis; Ann Epidemiol; 18(8); pp. 614-627 (author manuscript, 25 pgs printed); Aug. 2008.
Diffey et al.; The standard erythema dose: a new photobiological concept; Journal of Photodermatology, Photoimmunology & Photomedicine; 13(1-2); pp. 64-66; Feb./Apr. 1997.
Environmental Protection Agency; Ultraviolet and Ozone Monitoring Program (program information); retrieved Oct. 24, 2016 from the internet archive: (http://web.archive.org/web/20080516110808/http://www.epa.gov/uvnet/); last updated: Jan./Feb. 2008.
Fahrni et al.; Sundroid: Solar Radiation Awareness with Smartphones; Proceedings of the 13th Int'l. Conf. on Ubiquitous Computing (UbiComp '11); Beijing, China; pp. 365-374; Sep. 17-21, 2011.
Gerd Neumann Jr.; Deep-Black Optical Paint (product page); 1 pg.; retrieved from the internet: (http://www.gerdneumann.net/english/instrument-building-parts-teile-fuer-den-fernrohrbau/totmatte-schwarze-optikfarbe-deep-black-optical-paint.html) on Oct. 24, 2016.
Hartigan, John A.; Clustering Algorithms; John Wiley & Sons, Inc.; pp. 84-99; Apr. 1975.
Hartigan et al.; Algorithm AS 136: A K-Means Clustering Algorithm; Journal of the Royal Statistical Society. Series C (Applied Statistics); 28(1); pp. 100-108; 1979.
Heckman et al.; Minimal erythema dose (MED) testing; J. Vis. Exp.; 75; e50175; 5 pgs.; May 2013.
Heydenreich et al.; Miniature personal electronic UVR dosimeter with erythema response and time-stamped reading in a wristwatch; Photochem Photobiol.; 81(5); pp. 1138-1144; Sep./Oct. 2005.
Horsley et al.; Current action for skin cancer risk reduction in English schools: pupils' behaviour in relation to sunburn; Health Educ Res.; 17(6); pp. 715-731; Dec. 2002.
Indiegogo; SunFriend UV Daily Activity Monitor (product information); 8 pgs.; retrieved from the internet (https://www.indiegogo.com/projects/sunfriend-uv-daily-activity-monitor) on Oct. 19, 2016.
Klein et al.; Analysis of compact fluorescent lights for use by patients with photosensitive conditions; Photochem Photobiol; 85(4); pp. 1004-1010; (15 pgs., author manuscript version); Jul./Aug. 2009.
Larason et al.; Sources of error in UV radiation measurements; J. Res. Natl. Inst. Stand. Technol.; 106(4); pp. 649-656; Jul./Aug. 2001.
Lindgren et al.; Measuring effective vitamin D3-producing ultravioloet B radiation using Solartech's Solarmeter 6.4 Handheld, UVB radiometer®; Bull. Chicago Herp. Soc.; 43(4); pp. 57-62; 2008.
MacKenzie; The analysis of the ultraviolet radiation doses required to produce erythemal responses in normal skin; Br. J. Dermatol.; 108(1); pp. 1-9; Jan. 1983.
McKinlay et al.; A reference action spectrum for ultra-violet induced erythema in human skin; CIE J.; 6(1); pp. 17-22; Mar. 1987.
NASA; Actillume (hardware information page); 1 pg.; retrieved from the internet: (https://lsda.jsc.nasa.gov/scripts/hardware/hardw.aspx?hardware_id=173) on Oct. 21, 2016.
Natatmo; Be Sun Savvy: JUNE by netatmo (product information); 6 pgs.; Jan. 5, 2014 (product date: 2011).
Oren et al.; An Open Trial of Morning Light Therapy for Treatment of Antepartum Depression; American Journal of Psychiatry; 159(4); pp. 666-669; Apr. 2002.
pveducation.org; Spectral Irradiance; 1 pg.; retrieved from the internet: (http://www.pveducation.org/pvcdrom/2-properties-sunlight/spectral-irradiance); on Oct. 24, 2016.
Rabin; A portable glow to help melt those winter blues; New York Times (p. D5) 4 pgs.; Nov. 15, 2011.
Rensselaer, Lighting Research Center; Demesimeter—Light and Activity Measurement System Description and Calibration; 14 pgs.; Sep. 2, 2011 (rev. Nov. 15, 2011).
Rogers et al.; Prevalence and determinants of sunburn in Queensland; Health Promot J Austr.20(2); pp. 102-106; Aug. 2009.
Sayre et al.; Skin type, minimal erythema dose (MED), and sunlight acclimatization; Am. Acad. Dermatology; 5(4); pp. 439-443; Oct. 1981.
SBIR (STIR); Actillume—A monitor for activity and light exposure (research information); 2 pgs.; retrieved from the internet: (https://lsda.jsc.nasa.gov/scripts/hardware/hardw.aspx?hardware_id=173) on Oct. 21, 2016.
Schmalwieser et al.; A first approach in measuring, modeling and forecasting the vitamin D effective UV radiation; SPIE Proceedings; vol. 6362; Remote Sensing of Clouds and the Atmosphere XI, 63622C; Stockholm, Sweden; 9 pgs.; Sep. 11, 2006.
Solartech, Inc.; Radiometer UV Index: Model 6.5 (product information: SM/Sensors/Model 6.5 UV index_Sep. 2015); 2 pgs.; retrieved from the internet (http://www.solarmeter.com/model65.html) on Oct. 19, 2016.
Solartech, Inc.; Solarmeter Model 5.0 UV Meter; 2 pgs.; retrieved from the internet (http://www.solarmeter.com/model5.html) on Oct. 19, 2016.
Solartech, Inc.; Solarmeter Model 6.5 UV Meter; 4 pgs.; retrieved from the internet (http://www.solarmeter.com/model65.html) on Oct. 19, 2016 .
Sunsprite; Sunsprite Personal Light Tracker (product information); © 2016; 6 pgs.; retrieved from the internet (https://www.sunsprite.com/) on Oct. 19, 2016.
Thieden et al.; The wrist is a reliable body site for personal dosimetry of ultraviolet radiation; Journal of Photodermatology, Photoimmunology & Photomedicine; 16(2); pp. 57-61; Apr. 2000.
Weichenthal et al.; Phototherapy: how does UV work?; Photodermatol Photoimmunol Photomed.; 21(5); pp. 260-266; Oct. 2005.
Wikipedia; Bluetooth low energy; 11 pgs.; retrieved from the internet (https://en.wikipedia.org/wiki/Bluetooth_low_energy) on Oct. 21, 2016.
Wikipedia; Diffuser (optics); 2 pgs.; retrieved from the internet (https://en.wikipedia.org/wiki/Diffuser_(optics)) on Oct. 21, 2016.
Wikipedia; Lambert's cosine law; 4 pgs.; retrieved from the internet (http://en.wikipedia.org/wiki/Lambert's_cosine_law) on Oct. 21, 2016.
Wikipedia; Norm (mathetics): 3.2 Euclidean norm (definition); 10 pgs.; retrieved from the internet: (https://en.widipedia.org/wiki/Norm_(mathematics)#Euclidean_norm) on Oct. 24, 2016.
Wikipedia; Solar zenith angle; 2 pgs.; retrieved from the internet (https://en.wikipedia.org/wiki/Solar_zenith_angle) on Oct. 21, 2016.
Wirz-Justice; A randomized, double-blind, placebo-controlled study of light therapy for antepartum depression; J Clin Psychiatry; 72(7); pp. 986-993; Jul. 2011.
Dumont et al.; U.S. Appl. No. 15/247,829 entitled "Methods, Systems, and Apparatuses for Accurate Measurement and Real-Time Feedback of Solar Ultraviolet Exposure", filed Aug. 25, 2016.
Dumont et al.; U.S. Appl. No. 15/247,813 entitled "Methods, Systems, and Apparatuses for Accurate Measurement and Real-Time Feedback of Solar Ultraviolet Exposure", filed Aug. 25, 2016.
Dumont et al.; U.S. Appl. No. 15/247,819 entitled "Methods, Systems, and Apparatuses for Accurate Measurement and Real-Time Feedback of Solar Ultraviolet Exposure", filed Aug. 25, 2016.
Dumont et al.; U.S. Appl. No. 29/575,549 entitled "Sensing Device", filed Aug. 25, 2016.
amazon.com; UV meter (search results); 5 pgs.; retrieved from the internet (https://www.amazon.com/s/ref=nb_sb_noss_1?url=search-alias%3Daps&field-keywords=uv+meter) on Dec. 9, 2014.
Ferguson et al.; Voluntary exposure of some western-hemisphere snake and lizard species to ultraviolet-B radiation in the field: How much ultraviolet-B should a lizard or snake receive in captivity?; Zoo Biol; 29(3); pp. 317-334; May/Jun. 2010.
Zayat et al.; Preventing UV-light damage of light sensitive materials using a highly protective UV-absorbing coating; Chem Soc Rev.; 36(8); pp. 1270-1281; Aug. 2007.

* cited by examiner

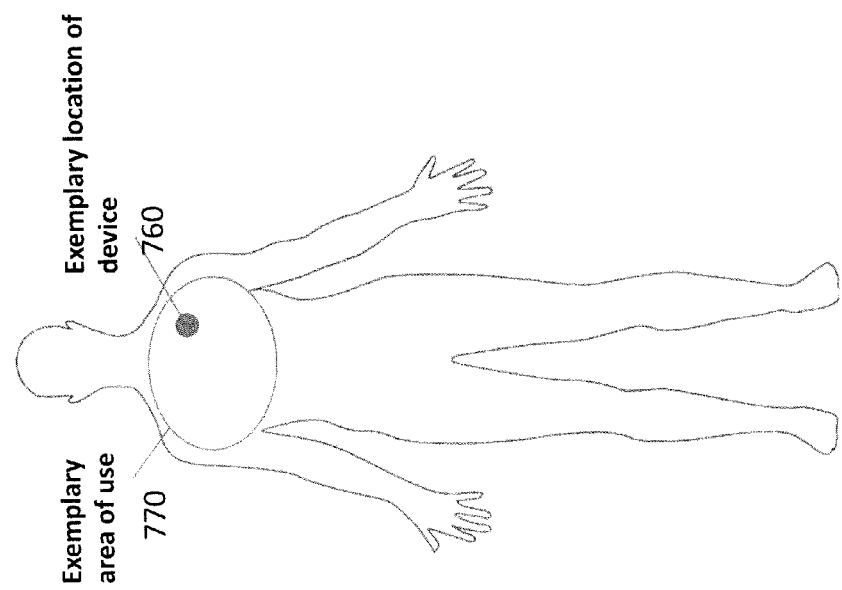
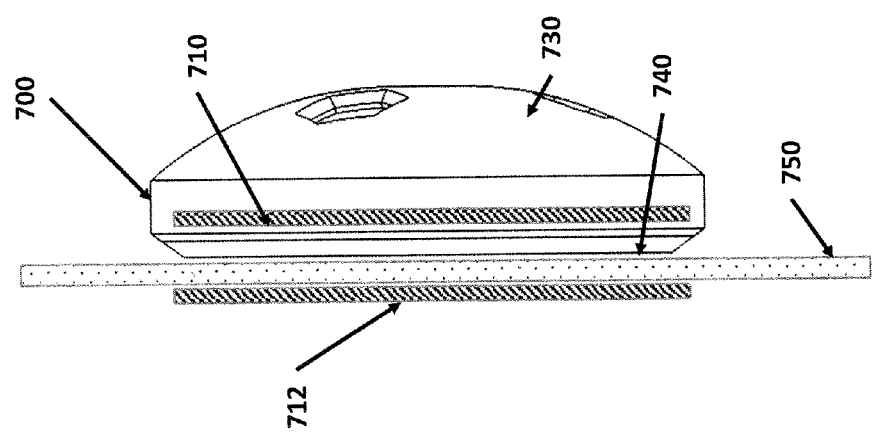
Figure 9(a)
Figure 9(b)

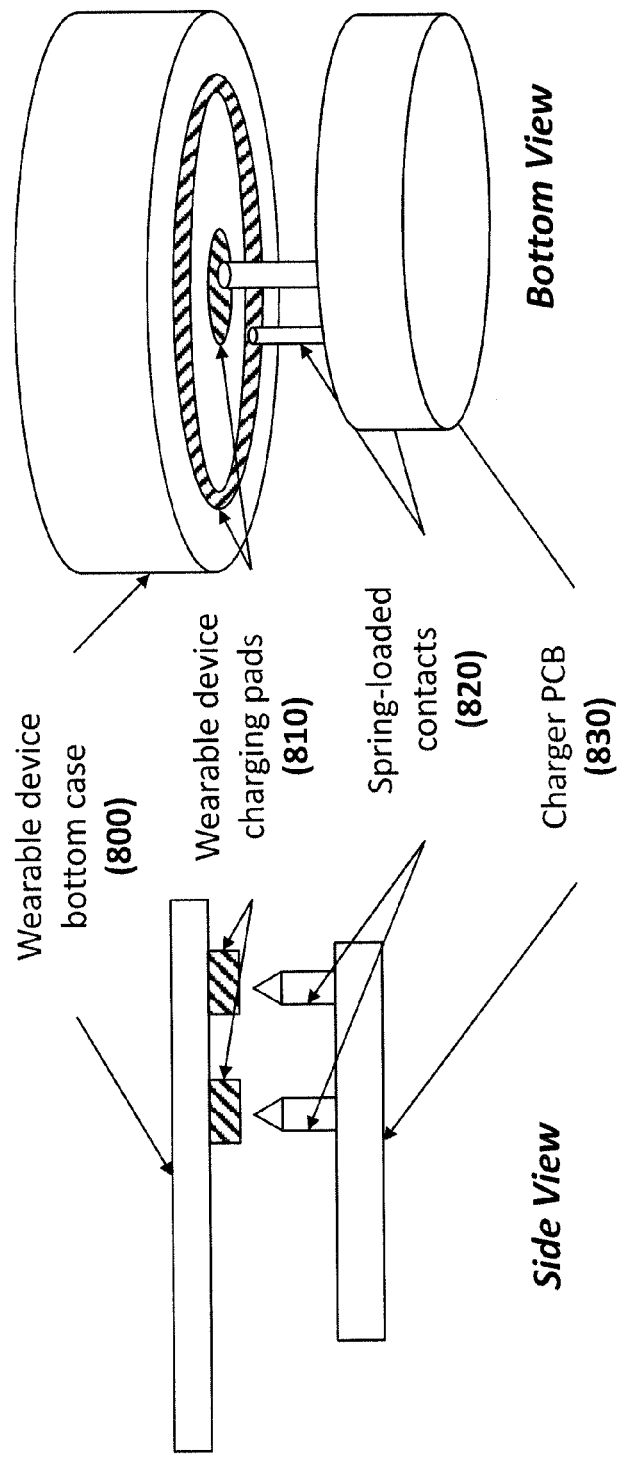
Figure 11B *Bottom View*
Figure 11A *Side View*

Figure 14(a)(ii)

METHODS, SYSTEMS, AND APPARATUSES FOR ACCURATE MEASUREMENT AND REAL-TIME FEEDBACK OF SOLAR ULTRAVIOLET EXPOSURE

CROSS REFERENCE TO RELATED APPLICATIONS

This application claims the benefit of the following three U.S. Provisional Applications, which are incorporated by reference herein: 62/209,813, filed Aug. 25, 2015; 62/233,173, filed Sep. 25, 2015; and 62/233,190, filed Sep. 25, 2015.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Ultraviolet ("UV") light is radiation in the wavelength range of 260-400 nm. It is part of the solar radiation that reaches the Earth, and has critical impact on humans. The skin synthesizes Vitamin D on exposure to UV which makes UV necessary for health. But overexposure to UV can cause adverse effects such as sunburn, systemic reactions in autoimmune diseases such as lupus, or pharmaceutical phototoxicity in the short term, and non-melanoma and melanoma skin cancer, skin aging, pharmaceutical photoallergy, photogenotoxicity, and photocarcinogenicity in the longer term ('adverse effects' thereafter). Sensitivity to UV varies from person to person, e.g., darker skin types scatter more UV in the top layers of skin and hence are at lower risk for sunburn. However, their skin synthesizes less Vitamin D than lighter skins. Sun-related activity also varies from individual to individual. Outdoor runners are more exposed to UV than indoor treadmill runners. Certain professions, such as construction, involve large exposure to UV on a daily basis, while office jobs involve lower UV exposure. Under such circumstances, the primary way to be able to control any adverse event of overexposure is to have an accurate knowledge of personal UV dose. This is what is achieved by the proposed exemplary systems and methods, where the wearable device measures UV exposure and aggregates it to compute the UV dose, while the mobile device displays metrics and alerts to the user based on this information. In alternative designs, the mobile device, which may be referred to herein as a "remote device," can process one or more signals and aggregate the information.

How to Measure Solar UV Radiation in a Way Relevant to Human Health?

In 1987, the human sensitivity to ultraviolet radiation was defined by Diffey and later adopted by the World Metereological Organization and the World Health Organization (McKinlay, A. & Diffey, B. "A reference action spectrum for ultra-violet induced erythema in human skin". *CIE J* 17-22 (1987)). This sensitivity is called the erythema action spectrum and gives exponentially more importance to high-energy photons. When measured on a horizontal surface, this standard metric is called the ultraviolet index (UV Index, or UVI).

What impacts human health is the integration of UV exposure over time, referred to herein as the "UV dose."

When the UV exposure is weighted according to the erythema action spectrum, the accumulated dose is called the "erythemal dose."

Some UV measuring systems include a UV measuring diode, which converts the incident ultraviolet radiation signal to electric current, coupled with additional circuitry. This can include an analog-to-digital converter (ADC), op-amp and microcontroller, such as is described in Amini N., Matthews E. J., Vandatpour A., Dabiri F., Noshadi H., Sarrafzadeh M., "A Wireless Embedded Device for Personalized Ultraviolet Monitoring," *International Conference on Biomedical Electronics and Devices*, pp. 200-205 (2009). Some examples of these systems are the Solarmeter® 6.5 UVI and the Genicom UV Index Meter. While such systems might be capable of approximately measuring UV, they are not accurate in a wide variety of situations, as has been reported in Correa, M. D. P. et al. "Comparison between UV index measurements performed by research-grade and consumer-products instruments." *Photochem. Photobiol. Sci.* 9, 459-463 (2010), and Larason, T. C. & Cromer, C. L. "Sources of error in UV radiation measurements". *J. Res. Natl. Inst. Stand. Technol.* 106, 649-656 (2001).

Why is Accuracy Important in UV Measurements?

Several diseases or pharmaceutical treatments are negatively or positively (up to a certain point) impacted by UV exposure. For instance, UV exposure is sometimes used in the treatment of psoriasis and the dose of UV exposure used in these treatments is well defined. On the other hand, going over a threshold of UV dose can trigger symptoms in lupus patients, phototoxicity for certain drugs, or erythema and sunburn of the skin. Some clinical experiments have found the threshold for erythema (Sayre, R. & Desrochers, D. "Skin type, minimal erythema dose (MED), and sunlight acclimatization". *Am. Acad. dermatology* 439-443 (1981); Heckman, C. J. et al. "Minimal Erythema Dose (MED) testing". *J. Vis. Exp.* e50175 (2013) doi:10.3791/50175) for instance but most UV dose threshold are unknown—and they vary from person to person. Even when UV dose thresholds are known, it is important to know current dose relative to such thresholds. Overestimation of UV dose can lead to less time outside, hindering the capacity of planning properly one's day. Underestimation can lead to longer periods spent while exposed to UV (whether it is in sunlight or in the shade), which can easily cause adverse effects. This makes accuracy of extreme importance in the measurement of UV dose. Since UV dose is the UV exposure integrated over time, it follows that accurately measuring UV dose implies also accurately measuring the UV exposure.

An approximate forecast for the maximum daily UV Index is usually provided by local weather services, but is largely inadequate for measuring personal UV exposure. Whether a person is in the shade, in direct sunlight, in indirect sunlight, this forecast is the same although actual UV exposure varies dramatically.

What are the Advantages of Real-Time Measurement of UV Dose?

The importance of thresholds is already known—whether it is for UV-induced lupus symptoms, pharmaceutical phototoxicity, or erythema and sunburn. If the UV dose threshold is being approached, or has been exceeded, this information needs to be conveyed to the user so that he/she can act on it immediately. Otherwise it can lead to adverse effects that might lead to hospitalization. It is for instance known that UV exposure has a systemic impact on lupus and evidence shows that lupus patients experience more flares in the summer than in the winter, as reported in Chiche, L. et al. Seasonal variations of systemic lupus erythematosus flares in southern France. *Eur. J Intern. Med.* 23, 250-254 (2012).

The Importance of Separating UVB from UVA

The clinical literature, whether it is looking at skin cancer, Vitamin D, photosensitivity, phototoxicity, photocarcinogenicity, differentiates between UVB (280-320 nm wavelengths) and UVA (320-400 nm wavelengths). This is because the two types of UV have different impact on the human physiology. The depth of penetration of UV light into the skin increases with increasing wavelength. While UVB is absorbed in the upper layer of the skin, UVA is able to travel further into the skin. For this reason, UVA, although less energetic than UVB, has a significant impact on autoimmune reactions and phototoxicity/photosensitivity. Both UVB and UVA can cause redness of the skin, drug-induced reactions, and trigger the immune system to react. Outside, under solar radiation, UVB rays burn the skin before UVA do. For these reasons, the medical community stresses the importance of differentiating UVB and UVA when a UV dose is reported.

Previous methods have discussed chemical methods for measuring instantaneous UV radiation, as well as accumulated UV dose, such as in U.S. Pat. No. 4,255,665 and U.S. Pat. No. 2,949,880. U.S. Pat. No. 8,829,457 and U.S. Pat. No. 5,148,023 describe electrical devices connected to a display unit capable of monitoring UV dose. The lack of a mobile device interface to interact with the device makes it less accurate since it cannot use information such as the location and local time for correction. It also has no notion of real-time feedback to the user. U.S. Pat. No. 9,068,887 is derived from "Amini," but additionally utilizes the knowledge of location (as obtained by the mobile device) to correct UV Index readings. Some drawbacks of the earlier references are that they fail to utilize detection of operating environment, or sensor orientation to correct UV Index readings. Other previous methods discuss using visible light to estimate UV exposure, such as U.S. Pat. No. 9,360,364. That disclosure does not explain how they estimate UV exposure based on visible light, an arduous task since UV exposure does not correlate with visible light. A prime example of this lack of correlation is overcast weather, where visible light and heat are reflected/scattered by the clouds, but UV is still largely transmitted. The disclosure in U.S. Pat. No. 9,360,364 would be inaccurate in such situations.

Real-Time Notifications

U.S. Pat. No. 6,426,503 and US20040149921 describe providing touch-based feedback (using vibration), or with an audible alarm, when safe exposure thresholds are reached. It does not use notification on the mobile device. U.S. Pat. No. 9,068,887 describes notifications on a mobile device, but requires the wearable to be constantly connected (wirelessly) to the mobile device.

Separation of UVA and UVB

US 20120241633 describes a method to measure UVA and UVB separately. This is a pure hardware method involving the use of a photodiode with either a UVA filter or a UVB filter. The described hardware allows only one type of a measurement at a time.

User-Selectable Safe Thresholds

U.S. Pat. No. 9,068,887 describes "user-programmed safe thresholds", which means users are able to select the safe amount of UV exposure that they are open to receiving. They use skin type information to select a default threshold for each skin type. The medical literature shows, however, that every person has a unique threshold. An exemplary system attempting to perform such measurements has previously been proposed in Amini. It includes a wearable device with sensors, which wirelessly communicates with a mobile device (such as a smartphone or tablet).

Improved methods, devices and systems are needed to overcome shortcomings of the approaches described above.

SUMMARY OF THE DISCLOSURE

One aspect of the disclosure is a computer executable method for user selection of UV dose thresholds, comprising: presenting, on a display of a remote device, a time history of a subject's UV dose; presenting, on the display of the remote device, a time history of information indicative of a subject's symptoms; presenting on the display a user-adjustable interface adapted to allow a user to select a UV dose threshold based on the time history of information indicative of the subject's symptoms.

In some embodiments the presenting steps present the time histories broken up into the same epochs of time, such as days, and optionally where the epochs of time are user-selectable.

In some embodiments the user-adjustable interface comprises at least one of a text field, a slider, and a selectable menu.

In some embodiments the method further comprises presenting a user input element that allows for the recordation of a patient symptom, wherein the symptom is recorded into the time history.

In some embodiments the selected UV dose threshold is input to a method that is adapted to indicate how much time the subject can remain in current conditions before reaching the UV threshold. The method can also include displaying on the remote device an amount of time before the subject will reach the UV threshold.

In some embodiments the presenting steps occur simultaneously.

One aspect of the disclosure is a computer executable method for estimating an amount of time for a subject to remain in an environment until they reach a limit of UV dose: receiving a current UV dose, a UV dose limit, and a current UV exposure, the current UV dose and current UV exposure based on sensed UV light from a wearable UV light sensing device; using the current UV dose, the UV dose limit, and the current UV exposure to estimate an amount of time before a subject will reach the UV dose limit; and displaying the amount of time or an indicator of the amount of time on a display of either the wearable device or the remote device.

In some embodiments estimating an amount of time comprises estimating UV exposure using an estimated maximum UV exposure, local sunset time, and local sunrise time. The method can also include estimating maximum UV exposure using the current UV exposure, sunrise time, and sunset time.

In some embodiments the method further comprises communicating an updated output indicative of an updated amount of time in response to an additional current UV exposure based on sensed UV light from the wearable UV light sensing device.

In some embodiments the method further comprises estimating the current UV exposure based on previous current UV exposures.

In some embodiments the method further comprises, in response to a determination that the subject is indoors based on a signal received from a visible light sensor in the UV sensing device, displaying an indicator to the subject indicating that the UV exposure to the subject has been reduced.

The disclosure also includes devices (wearable or mobile) on which any of the suitable computer executable methods herein can be stored. For example, a mobile device or a wearable device can include a storage device, the storage device storing any of the computer executable methods herein.

One aspect of the disclosure is a wearable UV sensing device comprising: a wearable housing that comprises a UV sensor and a proximity sensor, the proximity sensor comprising a proximity light detector adapted to detect reflected light from a proximity light source.

In some embodiments the proximity light source is an infrared light source, and the proximity detector is an infrared detector.

In some embodiments the UV sensor is a UVI sensor. The wearable housing can further include a UVA sensor.

In some embodiments the device also includes a visible light sensor. The proximity sensor and the light sensor can be part of the same sensor.

In some embodiments the UV sensor is disposed in a central region of housing, in a top view of the device, such as in the middle of the housing.

In some embodiments the proximity sensor is disposed closer to a periphery of the housing than the UV sensor.

In some embodiments the proximity sensor comprises the light source and the light detector. The light source can comprise an infra-red LED and the light detector can comprise an infra-red detector.

In some embodiments the device includes an orientation sensor.

In some embodiments the device further includes an optical diffuser disposed between a top housing layer and the UV sensor and proximity sensor.

The disclosure includes devices (wearable or mobile) on which any of the suitable computer executable methods herein can be stored. For example, a wearable device can include a storage device, the storage device storing any of the computer executable methods herein.

One aspect of the disclosure is a wearable UV sensing device comprising a UV sensor.

One aspect of the disclosure is a wearable UV sensing device comprising a proximity sensor.

One aspect of the disclosure is a wearable UV sensing device comprising a UVA sensor.

One aspect of the disclosure is a wearable UV sensing device comprising a visible light sensor.

One aspect of the disclosure is a wearable UV sensing device comprising a proximity sensor and a visible light sensor, and the proximity sensor and the light sensor can be part of the same sensor or they can be different sensors.

One aspect of the disclosure is a computer executable method of determining if a UV sensing device is at least partially covered, comprising: receiving information indicative of a signal from a proximity light detector that is disposed within a wearable UV sensing device, the information indicative of light reflected onto the proximity light detector from a proximity light source disposed in the wearable UV sensing device; determining, based on the information received, if the proximity light source is covered by a material; and sending a signal to a remote device to initiate an alert to a user of the determination that the proximity light source is covered and that the material should be removed from covering the proximity light source.

In some embodiments the determining step comprises characterizing an amount of light reflected onto the proximity light detector from the proximity light source. Characterizing an amount of light reflected onto the proximity light detector can comprise comparing the amount of light received with a proximity threshold.

One aspect of this disclosure is a computer executable method for automatically entering sleep mode on a wearable UV sensor (optionally stored in a storage device of a wearable UV sensor), comprising: receiving information indicative of a signal from a visible light sensor that is disposed in a wearable UV sensing device; using the information to determine if a condition of darkness adjacent the UV sensor has persisted for a period of time; and initiating a sleep mode for the wearable UV sensor if a determination has been made that a condition of darkness has persisted for a period of time.

In some embodiments using the information to determine if a condition of darkness adjacent the UV sensor has persisted for a period of time comprises: comparing the information with a visible light threshold; incrementing a counter if the information is not above the visible light threshold; and comparing counts from the counter with a threshold count, wherein the initiating step comprises initiating a sleep mode if the counts are greater than the threshold count.

In some embodiments the method further comprises maintaining an active mode of the UV sensing device if a determination has been made that a condition of darkness adjacent the UV sensor has not persisted for the period of time.

In some embodiments the method further comprises, after initiating sleep mode, initiating an active mode in which a UV sensor is activated based on the information indicative of a signal from the visible light sensor if the information is greater than a visible light threshold.

In some embodiments the method further comprises receiving information indicative of a signal from a proximity sensor in the UV sensing device and determining if a material covering the device is responsible for the condition of darkness.

In some embodiments initiating a sleep mode comprises decreasing the use of the UV sensor.

In some embodiments initiating a sleep mode comprises maintaining a use of the visible light sensor.

One aspect of the disclosure is a computer executable method of increasing the accuracy of UV monitoring (optionally stored on a device with a storage device), comprising: receiving UVB information that is indicative of an intensity of UVB light sensed by a UV sensor, the UV sensor disposed in a UV monitor; comparing the UVB information with a threshold UVB level to make a first determination if the UV monitor is indoors or outside; receiving secondary information indicative of light outside of the UVB range sensed by the UV sensor or a second sensor disposed in the UV monitor; using the secondary information to make a second determination about the environment of the UV monitor; using the second determination about the environment to select one of a plurality of environment models for predicting the UV Index; and predicting the UV Index with the selected model.

In some embodiments receiving secondary information comprises receiving secondary information indicative of visible light sensed by a second sensor, the second sensor being a visible light sensor disposed in the UV monitor, and wherein using the secondary information comprises using the secondary information to make a second determination about whether the UV monitor is outdoors and in the shade, or outdoors and in the open. Making the second determination can comprise comparing the secondary information indicative of visible light to a visible light threshold. The method can further include using the UVB information that is indicative of an intensity of UVB light sensed by a UV sensor and the secondary information indicative of visible light sensed by a second sensor to make a further determination about whether the UV monitor is in an open cloudy environment, or in an open and sunny environment. Making the further determination can comprise calculating if a polynomial is above an open threshold, the polynomial comprising a first variable indicative of the UVB information, and a second variable indicative of the visible light sensed by the second sensor.

In some embodiments receiving secondary information comprises receiving secondary information indicative of an intensity of UVA light, and wherein using the secondary information comprises using the secondary information to make a second determination about whether the UV monitor is indoors and in direct sunlight, or indoors and not in direct sunlight. Using the secondary information to make a second determination can comprise comparing the secondary information indicative of an intensity of UVA light to a UVA light threshold.

In some embodiments the computer executable method is stored in the UV monitor.

In some embodiments the computer executable method is stored in a remote device, the UV monitor and the remote device adapted to communicate.

In some embodiments the method further comprises presenting information on a remote device to the user, the information indicative of the predicted UV index.

In some embodiments receiving UVB information that is indicative of an intensity of UVB light sensed by a UV sensor can comprise receiving UVB information that is indicative of an intensity of UVB light sensed by a UVI sensor.

One aspect of this disclosure is a computer executable method of estimating UVA and UVB with a UVI sensor (optionally stored on a device with a storage device), comprising: receiving as input, from a remote device, a solar zenith angle; calculating a ratio comprising UVB and UVA using the solar zenith angle; receiving as input UVI information that is indicative of an output signal of a UVI sensor; calculating an estimated UVB using the UVI information and the calculated ratio comprising UVB and UVA; and calculating an estimated UVA using the UVI information and the calculated ratio comprising UVB and UVA.

In some embodiments the ratio is a function of the solar zenith angle.

In some embodiments the estimated UVB is used in calculating a time history of UVB exposure of a subject, further comprising presenting the time history of UVB on a display of the remote device.

One aspect of the disclosure is a computer executable method of modifying sensed UV signals based on orientation of a UV sensing device (which can be stored on a device with a storage device), comprising: receiving as input UV information indicative of UV light sensed by a UV sensor disposed in a UV sensing device; and estimating a UV irradiance incident normal to a face of a subject using an angle of tilt of the UV sensing device relative to a transverse plane of a subject, and the UV information, the angle of tilt derived from orientation sensor information from an orientation sensor disposed in the UV sensing device.

In some embodiments the UV information is indicative of UV light sensed by a UVI sensor.

In some embodiments the estimated UV irradiance is used in calculating a time history of UV exposure of a subject.

One aspect of the disclosure is a charging system for a wearable UV sensing device comprising: a wearable housing comprising a UV sensor, a central conductor, and at least one annular conductor extending around the central conductor, the central conductor and the at least one annular conductor at a bottom surface of the housing; a charger including at least first and second conductive contacts, wherein the first and second contacts are spaced from each other and the central conductor and annular conductor are spaced from each other such that the first and second contacts are aligned with the central conductor and the annular conductor, respectively, when the housing and charger interface.

In some embodiments the charger further comprises a first magnetic element that is magnetically attracted to a second magnetic element disposed within the wearable housing. The first and second magnetic elements can be positioned and configured such that their magnetic attraction facilitates the alignment of the first and second contacts with the central and annular conductors, respectively. The first and second magnetic elements can be substantially the same size.

In some embodiments the central conductor is, in a top view, aligned with the UV sensor.

One aspect of the disclosure is a wearable UV sensing system, comprising: a housing comprising a UV sensor and a first magnetic element; and a second magnetic element outside of the housing and adapted to have a magnetic attraction with the first magnetic element.

In some embodiments the second magnetic element is not physically attached to the housing.

In some embodiments the second magnetic element is physically attached to the housing.

In some embodiments the first and second magnetic elements have substantially the same shape. The first and second magnetic elements can have at least one dimension that is not the same.

In some embodiments the first magnetic element lies in a plane that is parallel with a bottom surface of the housing.

In some embodiments the first magnetic element is closer to the bottom surface than a top surface of the housing.

In some embodiments the UV sensor is closer to a top surface of the housing than the first magnetic element.

In some embodiments the first magnetic element, in a top view of the device, surrounds the UV sensor.

In some embodiments the first and second magnetic elements have annular configurations.

In some embodiments one of the first and second magnetic elements is a magnet and the other is a ferromagnetic material.

Some embodiments herein include systems, some of which include a wearable device and a mobile device (which may be referred to herein more generally as a "remote" device), which perform accurate measurement of UVA and UVB. In some embodiments the systems perform accurate measurement of UVA and UVB exposure on the human face, which is the region of the body the most exposed to UV. In some embodiments the wearable device comprises a unique combination of visible, UVA, UV Index and proximity sensors. The sensors can be covered by a diffuser with cosine response. In some embodiments a magnetic attachment system is adapted and configured to be attached to the front of a user's clothing. The disclosure includes algorithms, or computer executable methods, for estimating UVA and UVB from the data collected from these sensors, which can be corrected using knowledge of the environment around the user (e.g., shade or indoors), and/or the orientation of the device. The wearable device can also be made power efficient by using the visible light sensor to turn off operations at night. Some embodiments also include a real-time notification system, whereby the wearable is adapted to send an alert to the user's mobile device, even when the two are not connected wirelessly. In some embodiments the system is adapted to provide alerts (such as on the wearable device) in the case of events that affect measurement, such as when the device is accidentally covered. In some embodiments the system is adapted to predict the safe amount of time remaining to be spent in current conditions before a safety threshold is exceeded. These algorithms can take into account not only the current UV conditions, but also forecast UV conditions ahead to determine the safe time accurately. The predictions may take place on the mobile device or in some alternatives on the wearable device.

Figure 4:
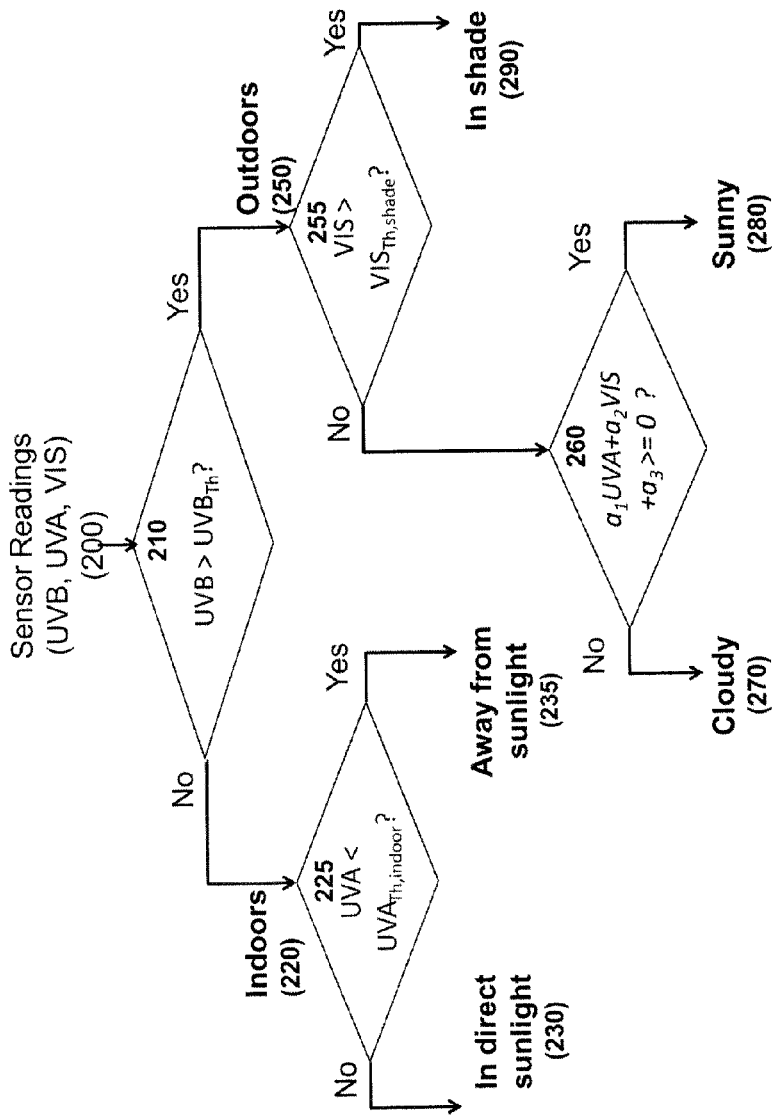

An exemplary algorithm for determining the environment based on sensor readings is shown in FIG. 4.

Figure 5:
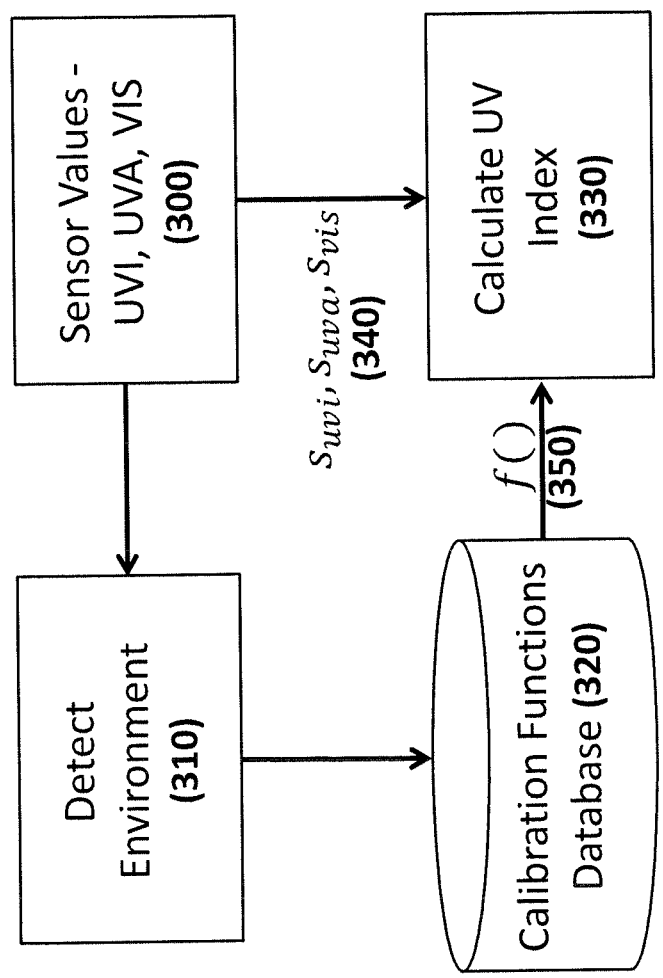

FIG. 5 is an exemplary method of selecting the appropriate model for predicting the erythemally-weighted UV exposure from the sensor values.

Figure 6:
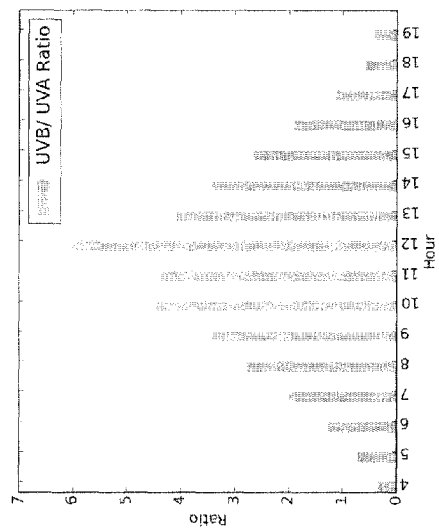

FIG. 6 shows the ratio of erythemally-weighted UVB to erythemally-weighted UVA as seen over the course of a day (every hour).

Figure 7:
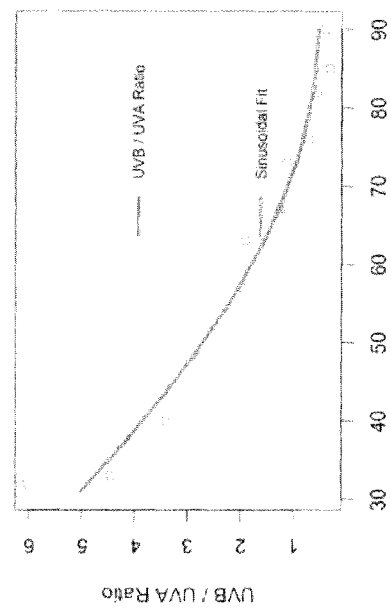

FIG. 7 shows the variation of $R_{B/A}$ with the solar zenith angle.

Figure 8:
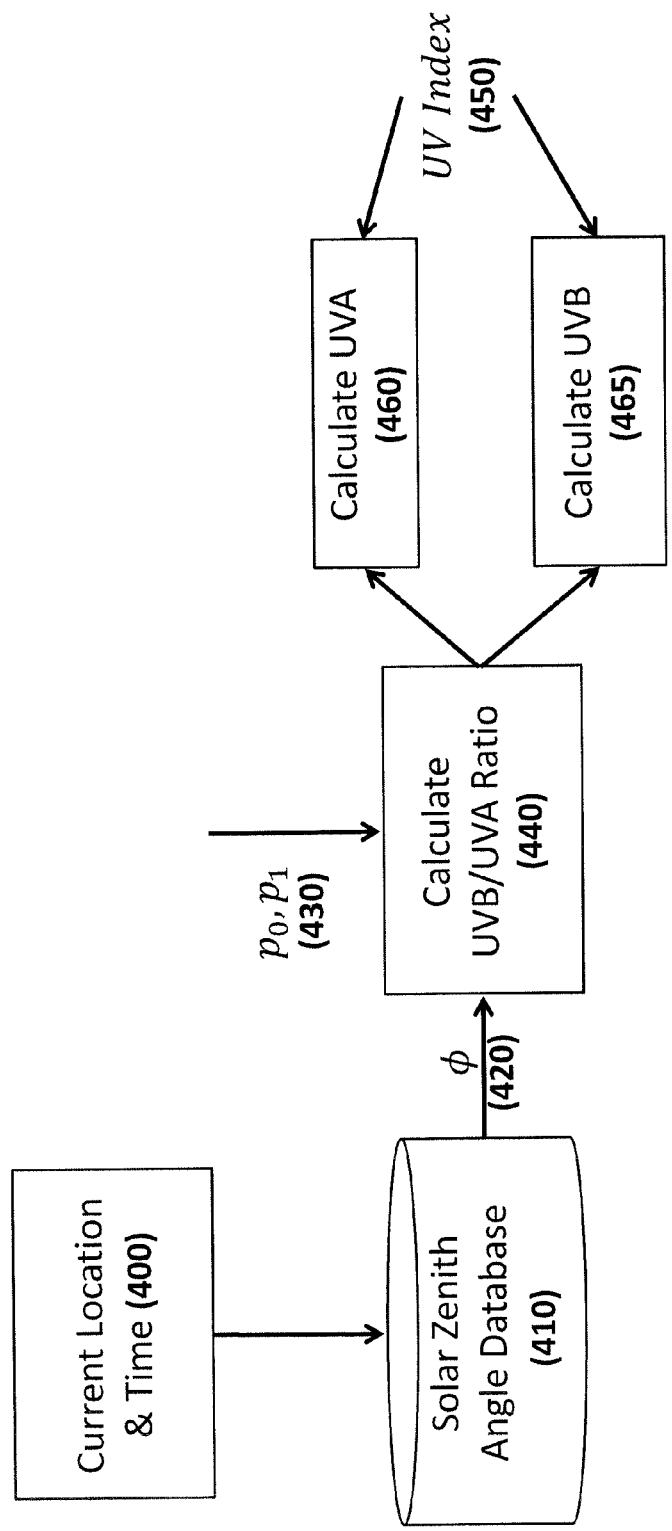

FIG. 8 shows an exemplary method for the estimation of UVA and UVB.

FIGS. 9A and 9B illustrate an exemplary magnetic attachment system.

Figure 10:
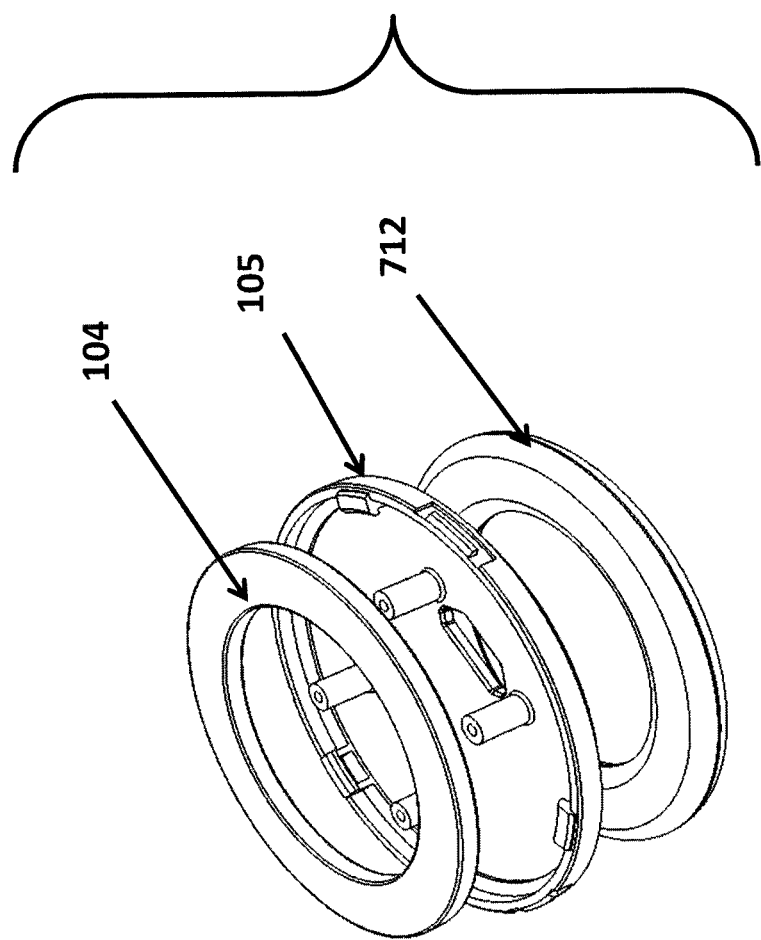

FIG. 10 illustrates an exemplary magnetic attachment system.

FIGS. 11A and 11B illustrate an exemplary charging system.

Figure 12B:
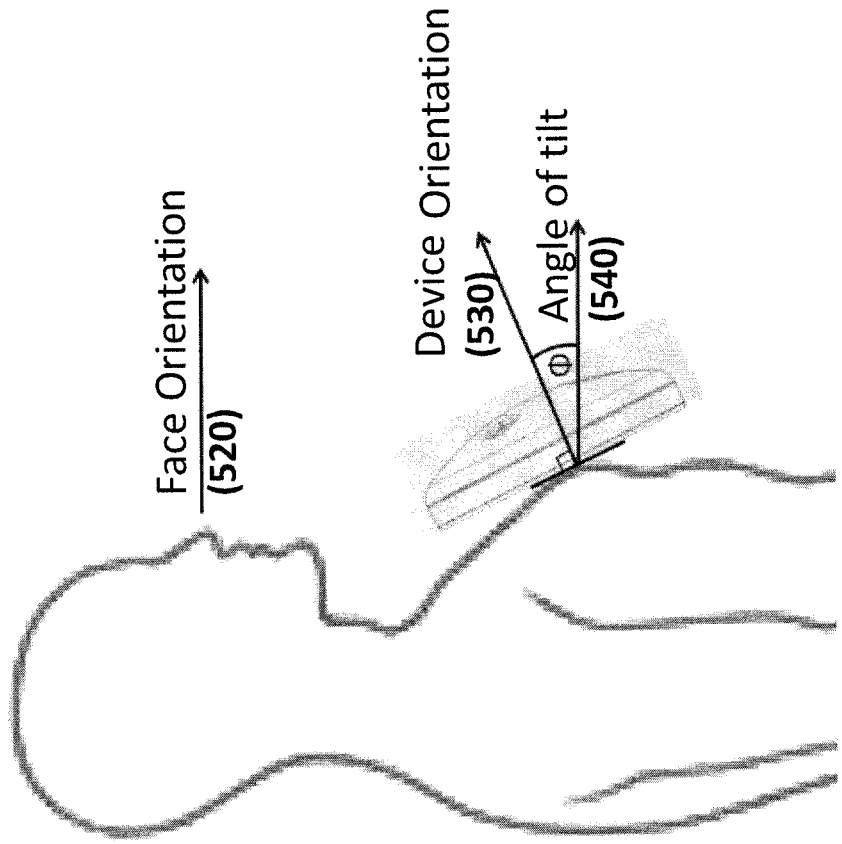
Figure 12A:
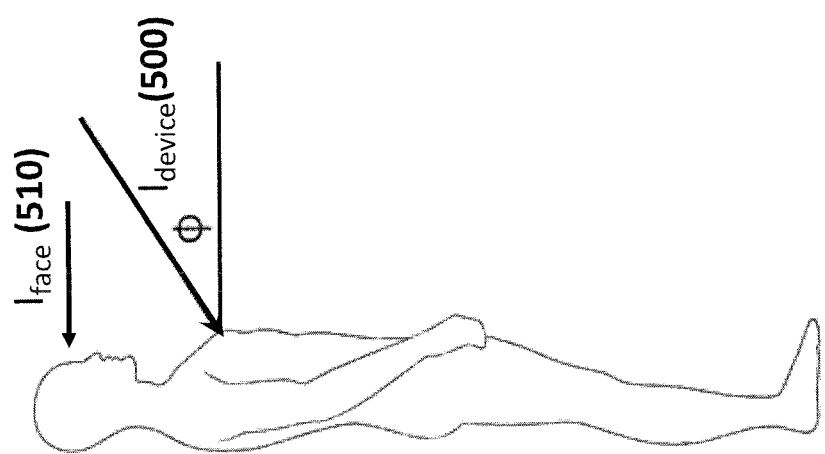

FIGS. 12A and 12B illustrate an angle the tilt ($\varphi$).

Figure 13:
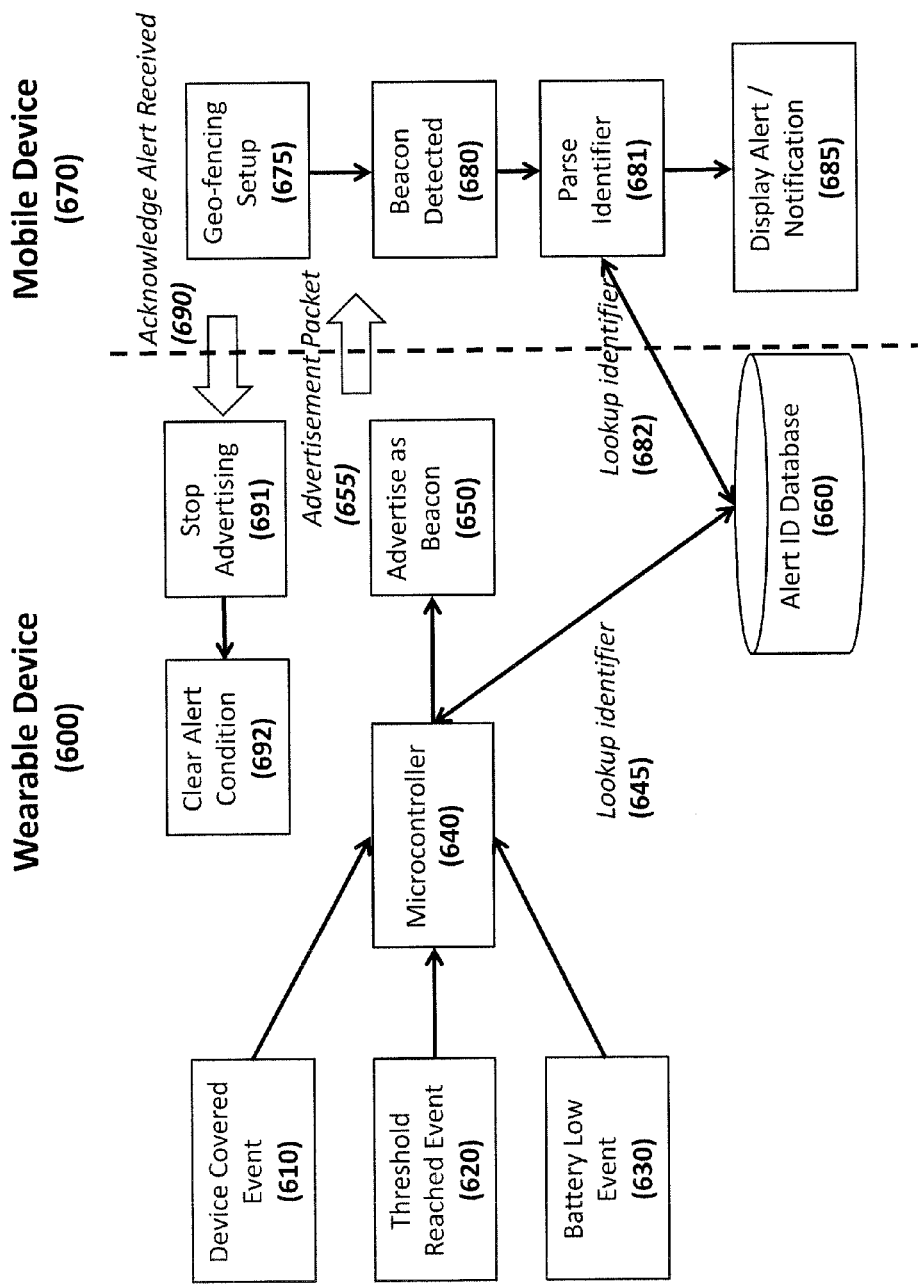

FIG. 13 illustrates an exemplary method of user notification.

Figure 14A:
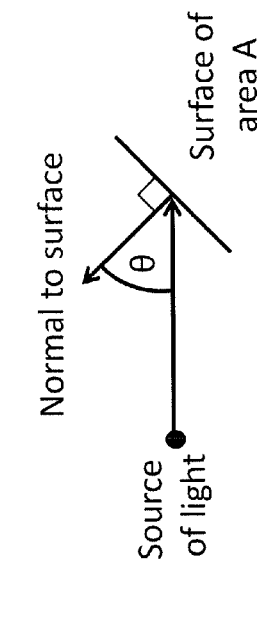

FIGS. 14(a)(i) and 14(a)(ii) illustrate light with and without a diffuser.

Figure 14B:
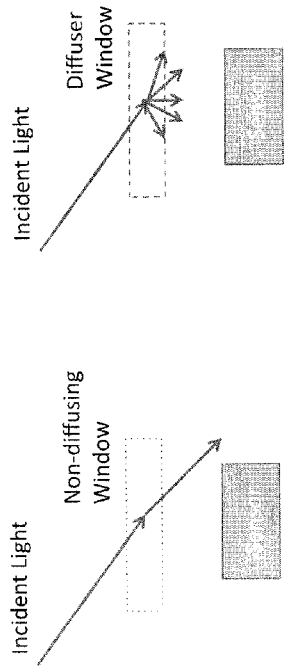

FIG. 14(b) illustrates the angle between a normal and the incoming ray of light.

Figure 15:
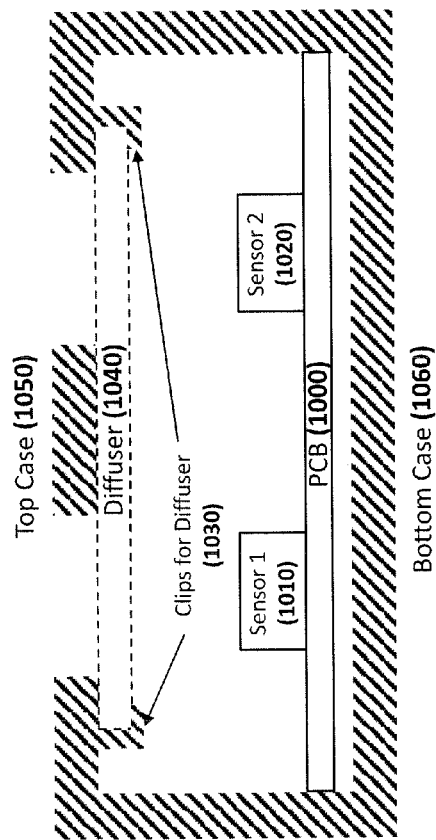

FIG. 15 illustrates an exemplary wearable device, including a diffuser therein and above a plurality of sensors also within the wearable device.

Figure 16:
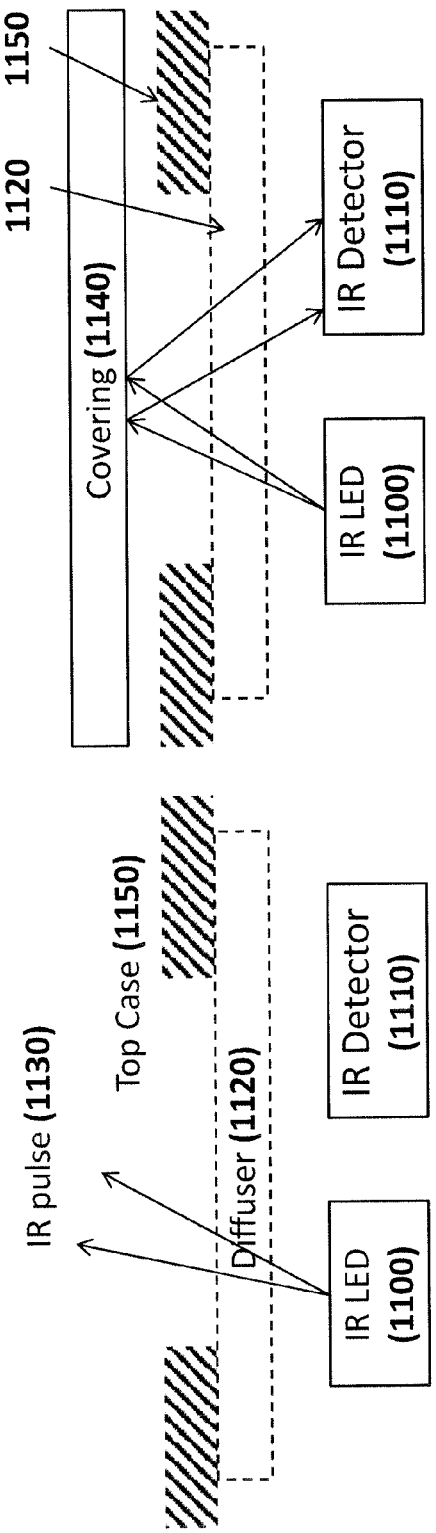

FIGS. 16A and 16B illustrate an exemplary proximity sensor, including a light source and a detector, and a covering material over the proximity sensor.

Figure 17:
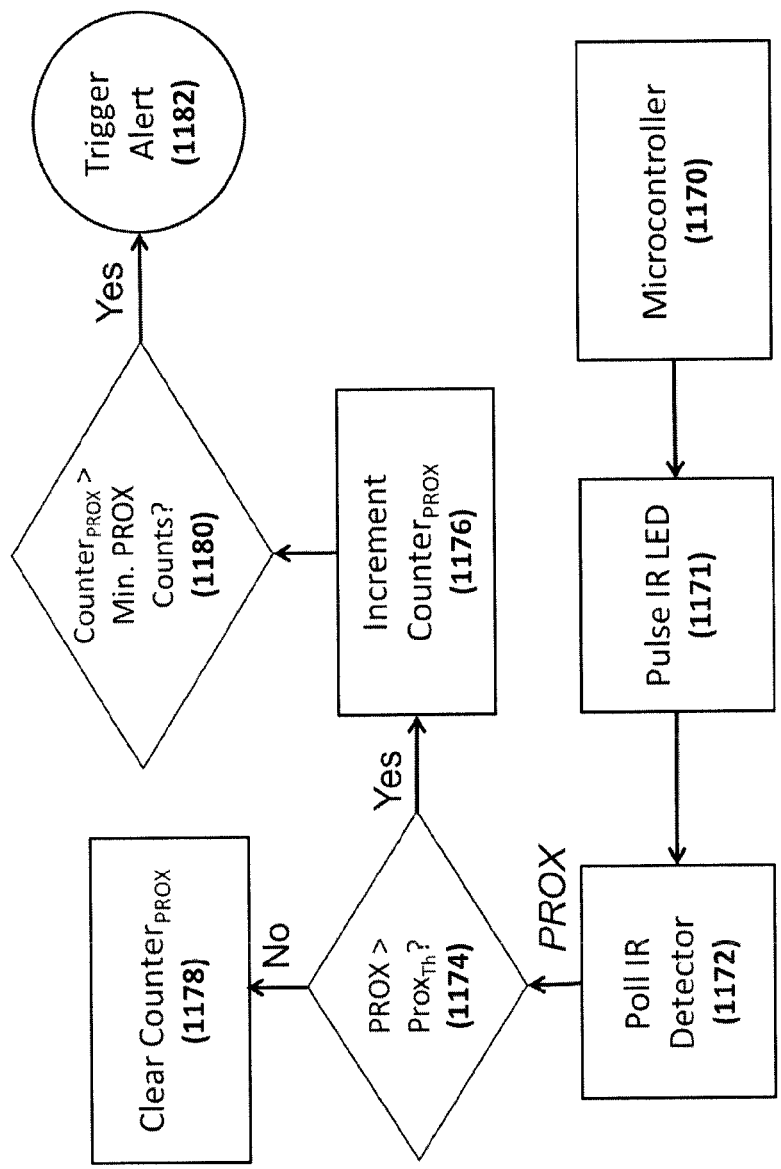

FIG. 17 illustrates an exemplary method for proximity detection using a proximity sensor.

Figure 18:
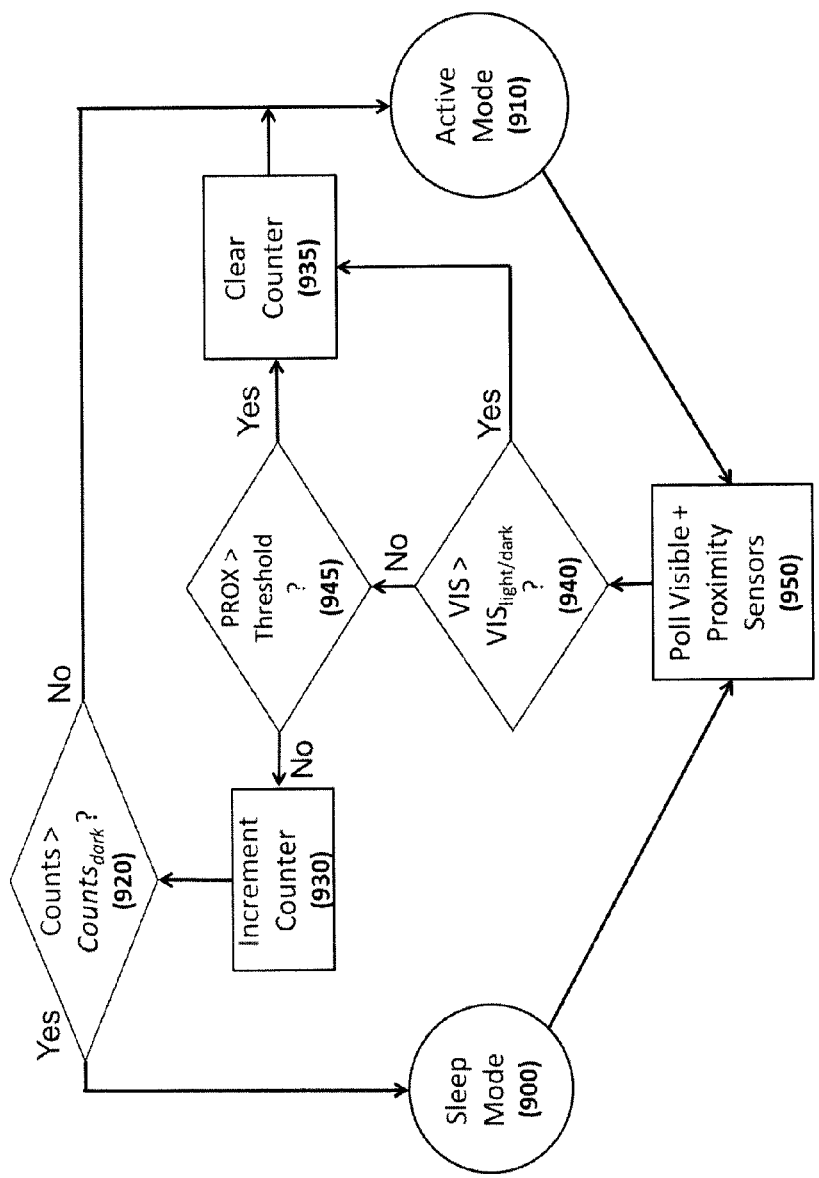

FIG. 18 illustrates an exemplary method that can cause a device to switch between a sleep mode and an active mode.

Figure 19B:
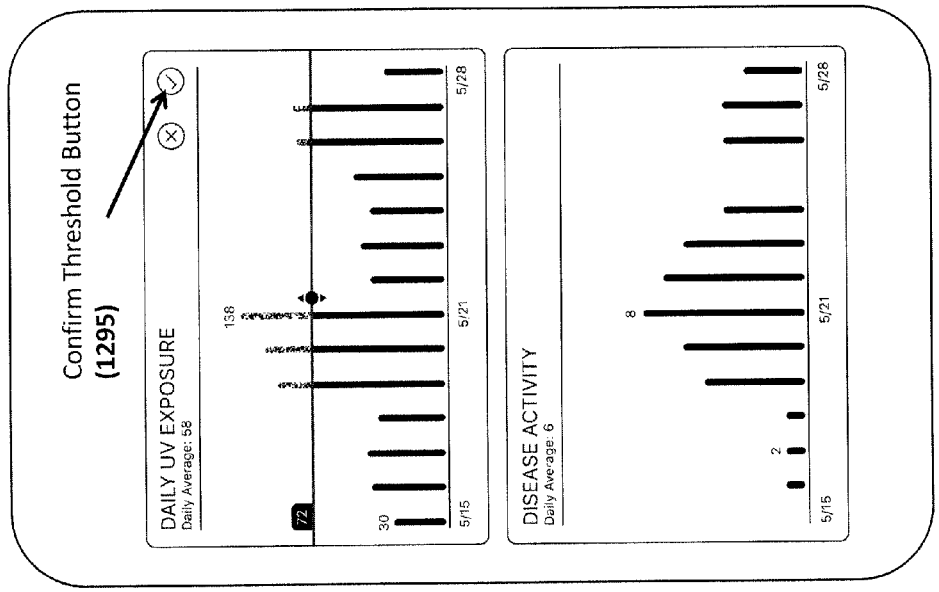
Figure 19A:
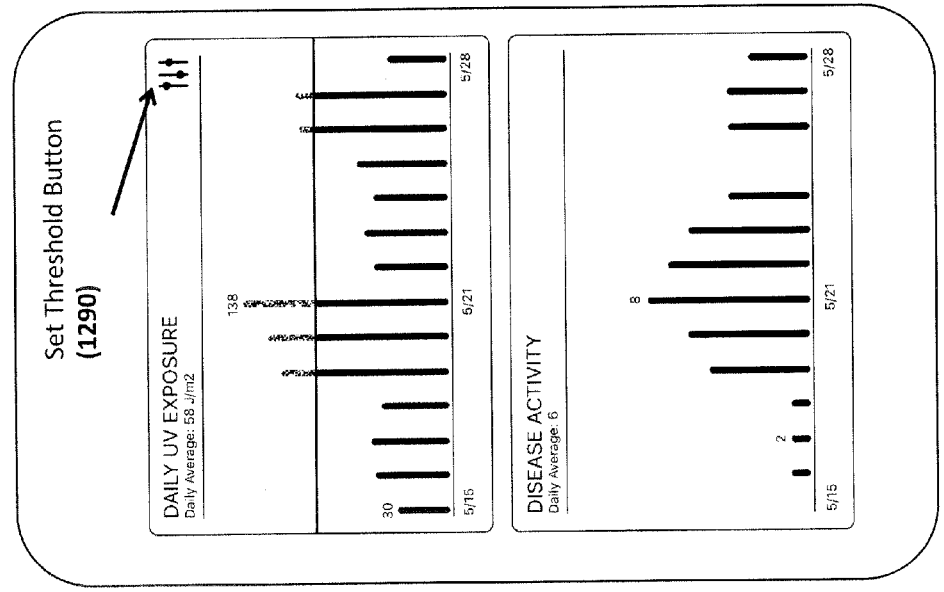

FIGS. 19A and 19B illustrate exemplary displays and a method of allowing users to select a UV threshold based on a time history of symptoms and UV exposure.

Figure 20:
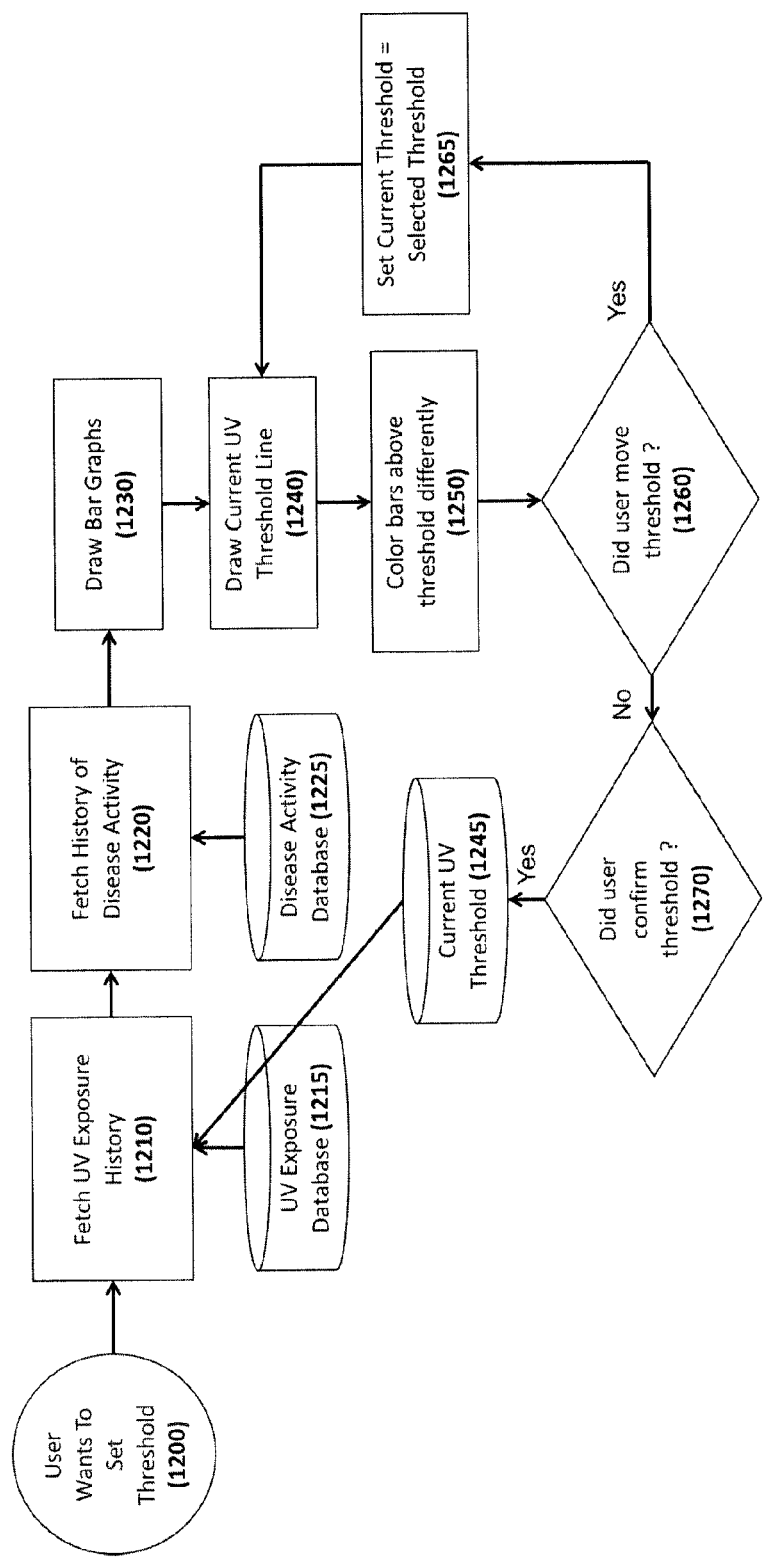

FIG. 20 illustrates an exemplary embodiment of a method for setting a threshold.

Figure 21:
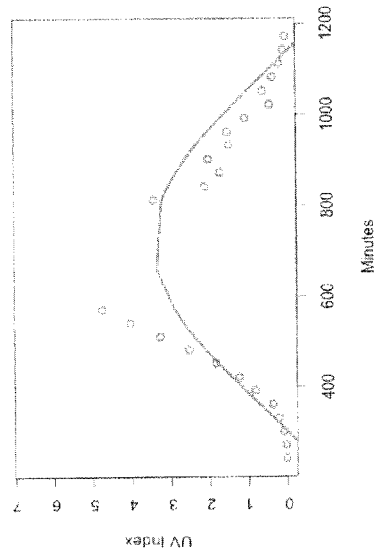

FIG. 21 shows the variation of UV index over a typical day.

Figure 22:
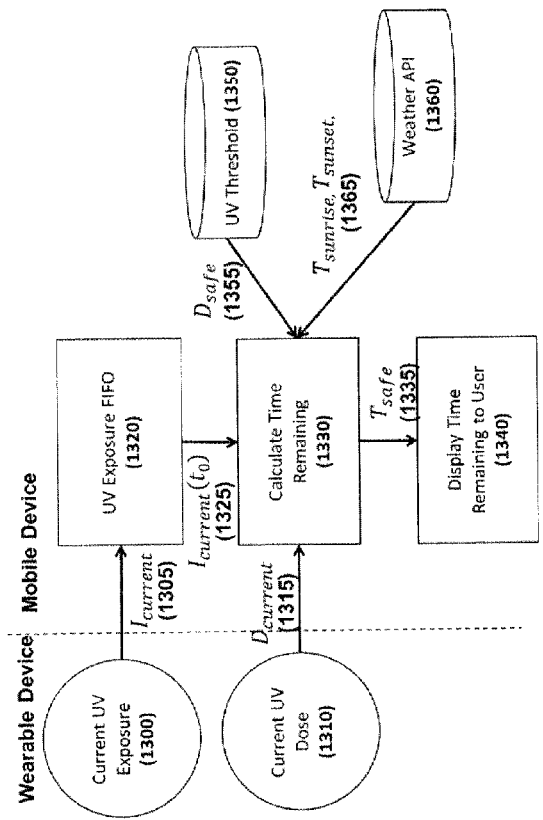

An exemplary computer executable method for estimating the safe amount of time to spend in current UV conditions is shown in FIG. 22.

DETAILED DESCRIPTION

The disclosure relates generally to methods, systems, and devices for UV sensing and estimation.

Figure 1:
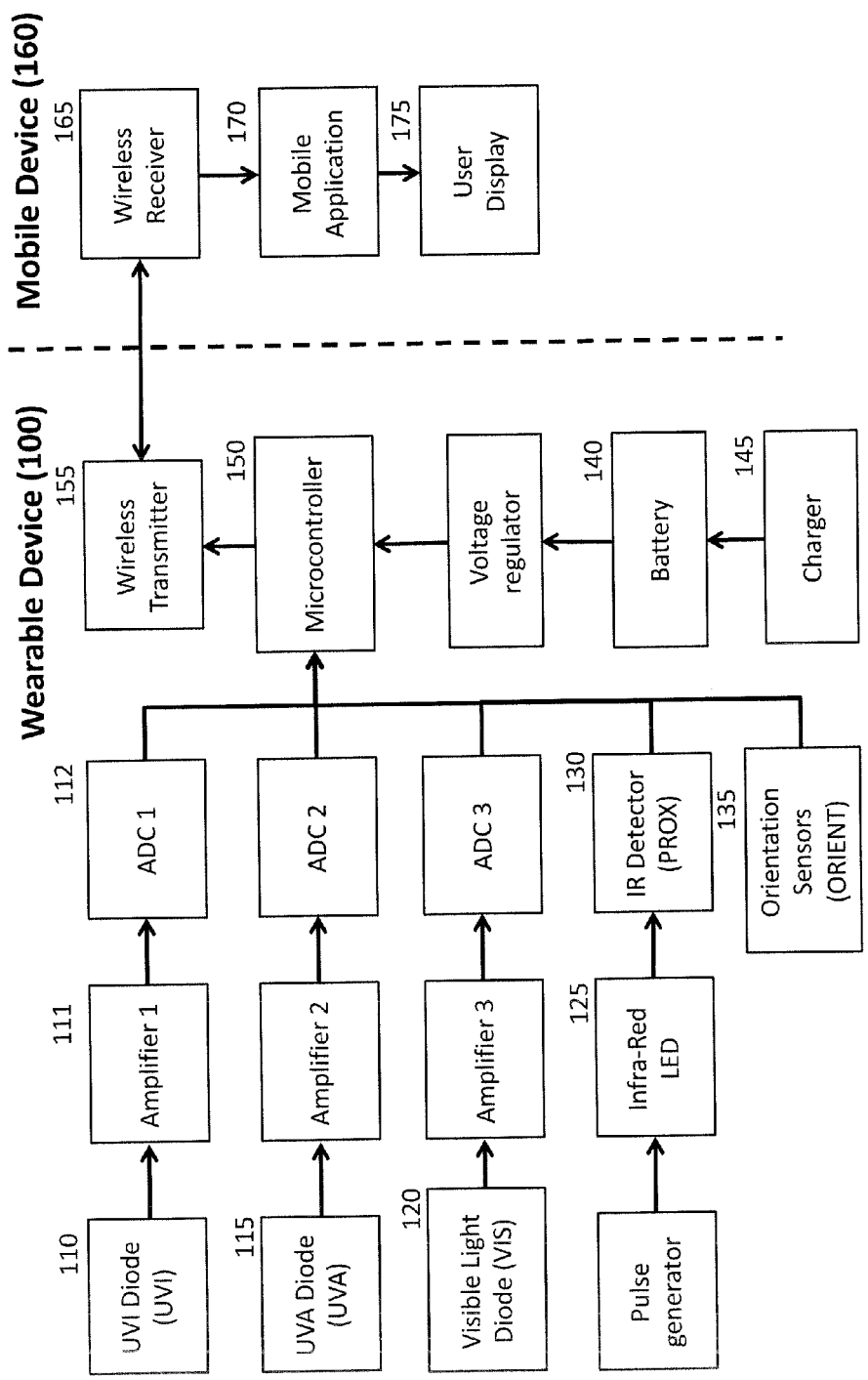
FIG. 1 illustrates an exemplary system including a wearable UV sensing device and a mobile device.

FIG. 1 is a block diagram of an exemplary system that can be adapted for accurate measurement and real-time feedback of ultraviolet exposure, and can incorporate any of the methods herein. The system in FIG. 1 includes two subsystems. The first subsystem is wearable device (100). Wearable device 100 includes a plurality of light sensors—a UV Index ("UVI") diode (110), a UVA diode (UVA) (115), a visible light diode (VIS) (120), an infra-red LED (125) coupled with an infra-red detector (PROX) (130). Additionally, the wearable device also includes one or more orientation sensors (ORIENT) (135) capable of determining the orientation of the wearable device in space. Sensors 110, 115, and 120 are in communication with a microcontroller (150) via one or more transimpedance amplifiers A1-A3, respectively (111), which itself is powered by an on-board battery (140). The battery is capable of being recharged via a charger (145). Microcontroller 150 transmits collected data via a wireless transmitter (155) following a certain protocol such as Bluetooth Low Energy, which is known.

The exemplary system in FIG. 1 includes a second subsystem—mobile device 160. The mobile device may also be referred to as a "remote" device. Mobile device (160) can be a typical handheld device such as a smartphone or tablet, which has a wireless receiver (165) that follows the same protocol as the transmitter on the wearable, e.g., Bluetooth Low Energy. Collected data is received by an application (170) executable on mobile device (160), which interfaces with the user via a display (175) that includes one or more pieces of information about the user's UV exposure. This display can be the screen of the mobile device.

Figure 2:
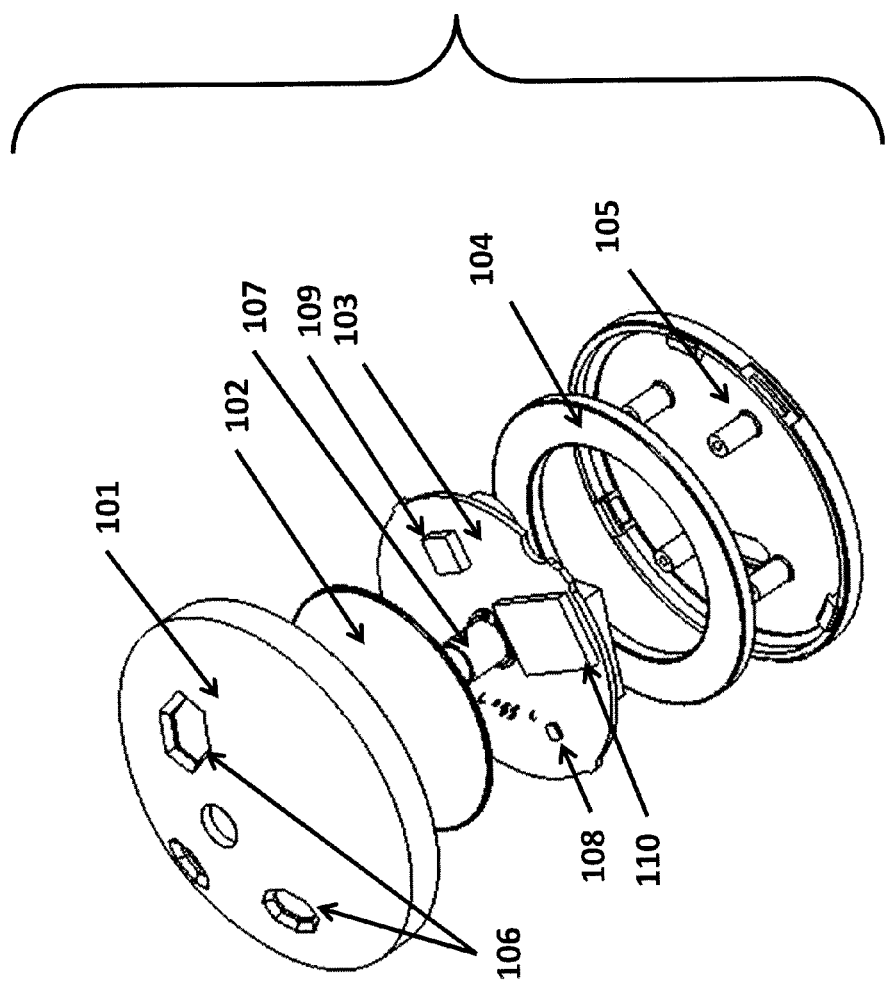
FIG. 2 is an exploded view of an exemplary wearable device.

An exploded view of an exemplary implementation of wearable device 100 is shown in FIG. 2. The wearable device includes a housing comprising top case 101 and bottom case 105, which contain therein internal components. Top case (101) is made of opaque material and has a plurality of windows 106 therein that allow light to reach the sensors that are disposed on a printed circuit board (PCB) (103) within the housing. In this exemplary embodiment, the device includes UVI sensor 107 disposed below the central window, proximity and visible light sensor 108 disposed below a peripheral window, UVA sensor 109 disposed below a second peripheral window, and a LED that cannot be seen in FIG. 2 because it is obscured by diffuser 107, but is disposed on printed circuit board 103 below a third peripheral window (the top window in the figure). In this exemplary embodiment the top case 101 includes a UVI sensor window, a UVA sensor window, a window for a sensor that includes both a proximity sensor and visible light sensor, and a LED light window, but in other embodiments it can have a different number of windows depending on how many objects disposed in the housing need to receive light, and their relative positions. Diffuser 102 is disposed between the top case 101 and the PCB 103, which is adapted to capture light from different angles and project them on to the sensors below. The PCB 103 rests on a magnet (104), which is optionally annular, which engages and attaches to the bottom case (105). The bottom case and the top case are secured to one another. The magnet can be is used in an attachment system, examples of which are described herein, wherein an external magnet allows the wearable device to be clipped on to any article of clothing. Microprocessor 110 is also shown on PCB 103.

The exemplary system has a unique combination of sensors: a UVI sensor, a UVA sensor, a visible light sensor, a proximity sensor, and an orientation sensor, as well as unique algorithms that can utilize information from one or more of the sensors. The following sub-sections describe how the sensors and algorithms can all work, some individually and some together, to improve either the accuracy of measurement or real-time feedback of ultraviolet exposure. Not all of the algorithms described herein need to be performed with each other. In fact, any of the algorithms herein can be used individually.

Figure 3:
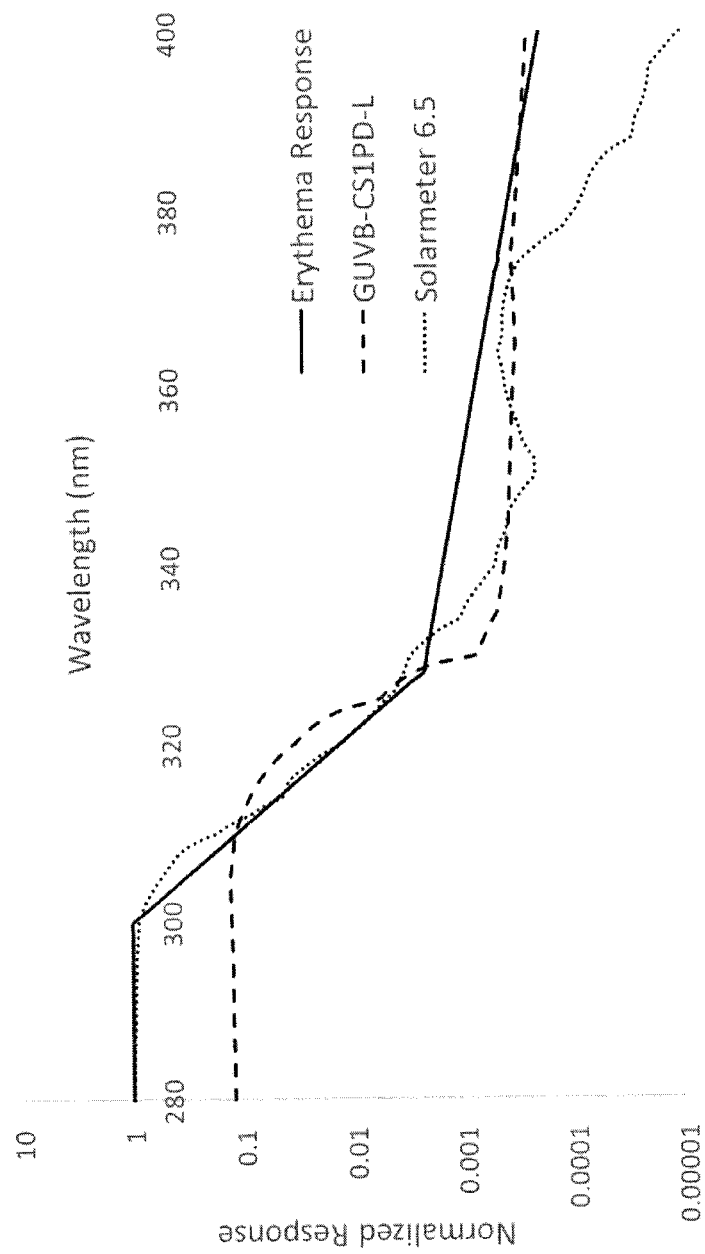
FIG. 3 shows the response of two commercially available UVI diodes and sensors in comparison to the erythema action spectrum.

The UVI, UVA and visible light sensors are all light sensors, but they have different responses to light. The optional UVA diode, examples of which are known, has a peak of measurement in the UVA region (315-400 nm) and has very low response outside this band. Similarly, the visible light diode, examples of which are known, has a peak of response in the visible light region (400-800 nm), and near-zero response outside this band. The UV Index (UVI) diode has a unique response that attempts to match the erythema action spectrum (see McKinlay, A. & Diffey, B. "A reference action spectrum for ultra-violet induced erythema in human skin". *CIE J.* 17-22 (1987)) by weighting the UVB (280-315 nm) exponentially higher than the UVA (315-400 nm), to mimic the impact of UV on the human body. This measurement is called erythemally-weighted UV. FIG. 3 shows the response of two commercially available UVI diodes and sensors in comparison to the erythema action spectrum.

In alternative embodiments, however, not all of the UVI, UVA, proximity, visible, and orientations sensors are included in the wearable device. For example, a UVA sensor is optional if information from a UVA is not needed for a particular method. Similarly, a visible light sensor is optional if an algorithm need not receive information from a visible light sensor. In some embodiments the device does not include an orientation sensor if the orientation is not needed or desired.

A previous experiment (E. Thieden et al., "The wrist is a reliable body site for personal dosimetry of ultraviolet radiation", *Journal of Photodermatology, photoimmunology & photomedicine*, Vol. 16, Issue 2, 2000) has observed that there is poor correlation between measurements of UV exposure on different parts of the human body (e.g., measuring on the wrist correlates poorly with measuring on the top of the head). Since a primary goal of the disclosure herein is accuracy of UV index estimation, the systems herein generally measure UV exposure on a specific part of the body only. For UV-sensitive patients, long-sleeved clothing and long pants cover most of the body from UV exposure, but the face is usually left exposed (since no one wears a mask in broad daylight). Therefore, in some embodiments, the system is adapted to accurately measure UV radiation dose incident on the face. The following subsections will list several characteristics of exemplary systems that can enable this.

1. Real-Time Correction Using Environment Detection

Measurement of erythemally-weighted UV (UV Index) from the solar spectrum is very prone to error. One of the primary factors affecting the accuracy of measurement is the environment in which the device is being used. Broadly speaking, there are two usage environments—indoors (220) and outdoors (250). Indoors can be further subdivided as being in direct sunlight 230 (through windows), or away from sunlight 235. Outdoor environment can be characterized as being in the open or in the shade 290. The open can be separated into sunny 280 or cloudy 270. Since the sensors are usually calibrated for only one type of environment, they will be erroneous when used in other types of environments. It is thus important to identify the environment and correct the output of the sensors accordingly, depending on the environment.

This exemplary system identifies the following environments:

(a) Indoors (220), in direct sunlight through windows (230)

(b) Indoors (220), away from direct sunlight (235)

(c) Outdoors (250), in shade (290)

(d) Outdoors (250), in the open with sunny weather (280)

(e) Outdoors (250), in the open with cloudy weather (270)

An exemplary algorithm for determining the environment based on sensor readings is shown in FIG. 4. This is a decision tree algorithm based on the readings from the UVI, UVA and visible light sensors (200). The next section will describe how these sensors are used to separately estimate erythemally-weighted UVA and UVB, but for this section it is assumed that the values have already been derived. We know that UVB is absorbed by glass and hence drops to undetectable levels when indoors. The same is not true for UVA, which is usually transmitted through glass. Thus, at the first level of the decision tree, we utilize the UVB value in comparison to a threshold $UVB_{th}$ to determine if the user is indoors or outdoors (210). The value of the threshold is trained a priori by collecting data from several users in both indoor and outdoor situations. A maximal margin separating hyperplane method (e.g., Cortes, C.; Vapnik, V. (1995). "Support-vector networks". *Machine Learning* 20 (3): 273. doi: 10.1007/BF00994018) can be used to train this threshold from the collected data.

If the user is determined to be indoors, the algorithm then utilizes the UVA sensor value to decide if the user is in direct sunlight through the windows or away from it. The algorithm then compares this UVA sensor reading to a threshold $UVA_{th,indoor}$, (225) which can be set using the same set of machine learning methods described above. It is known that UVA partially travels through windows, which makes the UVA value higher when in sunlight through the windows, and lower when away from the window.

If the algorithm determines the user is outdoors, the algorithm utilizes the reading of the visible light sensor (VIS) to determine if the user is in shade or in the open. The algorithm then compares the reading from the VIS sensor to a threshold $VIS_{th,shade}$ (255). Being lower than the threshold implies shade, while being above the threshold indicates being in the open. This threshold can be trained using data collected from a number of users in both situations. Finally, if in the open, the sensor values can further be utilized to determine whether the weather is cloudy or sunny. This is achieved using both the visible light readings (VIS) and the UVB reading (260). We know that clouds attenuate the visible light, but transmit UVB, while in sunny weather both VIS and UVB are high. We formulate this determination of cloudy vs. sunny as an optimization problem, where:

Environment=Cloudy, if $a_1 UVB + a_2 VIS + a_3 < 0$

=Sunny, if $a_1 UVB + a_2 VIS + a_3 \geq 0$

The parameters $a_1$, $a_2$ and $a_3$ can be trained using data collected with the devices placed in sunny and cloudy conditions. A maximal margin separating hyperplane algorithm (also known as a support vector machine) can be used to determine the optimal value of these coefficients. The above sunny vs. cloudy determination has been described as a two-class problem, but it can also be described as a multi-class problem to detect different cloud densities e.g., scattered light clouds vs. overcast. Solving such a multi-class problem would involve training several one-vs-all classifiers—one for each class that we are interested in.

Once the environment is detected, the device is able to select the appropriate model for predicting the erythemally-weighted UV exposure from the sensor values—FIG. 5. We refer to it as the UV Index, although strictly speaking the UV Index is for horizontal measurements and the device presented here has an orientation similar to the user's face. The UV Index is modeled as a polynomial function of the UVI, UVA and VIS sensor values ($s_{uvi}$, $s_{uva}$, $s_{vis}$):

$$UVIndex = f(s_{uvi}, s_{uva}, s_{vis})$$

The form of the polynomial function is derived during the calibration process. If we fit only one calibration function or model (f) for all environmental conditions, it suffers from a lack of accuracy. For example, a model that is calibrated on data collected across a variety of environments will not be particularly accurate for just the indoor environment. However, using multiple models, each of which is calibrated to data from a particular environment allows each model to be more accurate for only its particular environment. This exemplary embodiment uses five such models, corresponding to our five environments described above, which is stored in a calibration database (320). When the environment is detected (310) using our aforementioned decision tree algorithm, the system is able to select the most appropriate calibration function (350), which is then used with the sensor values (300) to derive the UV Index (330). This gives the most accurate measurement of the UV Index in all possible environments. The UV Index can then be, for example, displayed to a user on a display.

2. Separation of UV Measurement into UVA and UVB

The importance of separating UV dose measurement into UVA (320-400 nm wavelength) and UVB (280-320 nm wavelength) has already been elucidated. UVA has very different impact on the human body as compared to UVB. Different amounts of UVA and UVB are required for activation of an adverse response, with the amount of UVB being much smaller than UVA for the same adverse response. To weigh the consequences of UVB and UVA on an equal footing, it suffices to compare erythemally-weighted UVB and UVA. Here we describe two exemplary methods to measure erythemally weighted UVA and UVB dose—one utilizing two UVI diodes with different filters, the other utilizing software-based estimation with a single UVI diode.

In the first method, two diodes with identical response similar to the erythema spectrum are placed in the wearable device, one underneath a filter that lets pass the UVA region of the spectrum and nothing else, the other one underneath a similar filter for UVB. Since perfect filters for the said regions of the spectrum do not exist in practice, this method introduces errors, the first consequence of which is that the addition of the responses of both diodes (even when normalized to the peak transmission of each individual filter) may not be equal to the full erythema spectrum, hence the UVI cannot be retrieved from this device, even if the response curve of the original diodes were to match perfectly the erythema curve.

Another embodiment of the above concept makes use of diodes with different responses each, and also different filters. The combination of each diode response and filter tries to match as closely as possible the UVA portion of the erythema spectrum in one case, and the UVB in the other.

In either case, this configuration utilizing two diodes resembles that of the UVA and UVI diodes in FIG. 1, in that each is connected to an analog amplifier, then analog to digital converter and then the response is read in the microcontroller.

The above method has the drawback of utilizing two diodes, which makes it take up more area and increases expenses. We propose an alternative scheme for separating UVA and UVB dose estimation using a single UVI diode, coupled with a mobile device which has knowledge of the current location and local time. FIG. 6 shows the ratio of erythemally-weighted UVB to erythemally-weighted UVA as seen over the course of a day (every hour). Erythemal weighting gives exponentially higher weight to UVB as opposed to UVA, but the solar spectrum also contains much higher quantities of UVA as compared to UVB. The plot shown is for a location in France in summer. This ratio varies with location (latitude in particular), as well as time of the year. There are lower amounts of UVB during winter, and higher amounts during summer.

The erythemally weighted UVB/UVA ratio ($R_{B/A}$) is modeled as a function of solar zenith angle ($\varphi$). FIG. 7 shows the variation of $R_{B/A}$ with the solar zenith angle. We fit a sinusoidal function to this data, which allows us to model the UVB/UVA ratio as a function of the solar zenith angle.

$$R_{B/A} = p_0 + p_1 \sin \varphi \qquad (Eq.\ 2.1)$$

The flow for estimation of UVA and UVB using this method is shown in FIG. 8. The mobile device, such as mobile device 160, has information about the current location and time of the measurement (400). This is used to look up the solar zenith angle for an existing database (410). The solar zenith angle (SZA) is readily available via internet APIs or can be computed using well-known models. With knowledge of the SZA ($\varphi$) (420), and the coefficients $p_0$, $p_1$ (430), we calculate the UVB/UVA ratio using Eq. 2.1 (440). The system then estimates in real time, the amount of erythemally-weighted UVB (EUVB) and erythemally-weighted UVA (EUVA) separately (460, 465) from the UV Index (450) using the following equations:

$$EUVB = 25\frac{mW}{cm^2} UVIndex \frac{R_{B/A}}{1 + R_{B/A}} \qquad (Eq.\ 2.2)$$

$$EUVA = 25\frac{mW}{cm^2} UVIndex \frac{1}{1 + R_{B/A}} \qquad (Eq.\ 2.3)$$

The factor of 25 accounts for the fact that one unit of UV Index corresponds to 25 mW/cm$^2$ of erythemally weighted ultraviolet radiance (McKinlay, A. & Diffey, B. "A reference action spectrum for ultra-violet induced erythema in human skin". *CIE J* 17-22 (1987)). The UVA and UVB estimate can then be used in any methods herein, such as estimating the UV index.

3. Magnetic Attachment Method

Ultraviolet exposure on one region of the body often does not correlate with other regions. For example, E. Thieden et al., "The wrist is a reliable body site for personal dosimetry of ultraviolet radiation", *Journal of Photodermatology, photoimmunology & photomedicine*, Vol. 16, Issue 2, 2000, found that exposure on the chest does not correlate well with the top of the head, so measuring one does not give a clear idea of the other. The systems herein are generally configured and adapted to measure ultraviolet dose on the face. We observe that other portions of the body can be adequately shielded with clothing options such as long-sleeved shirts, trousers and shoes, but the hands and the face are the most difficult to shield due to lack of sufficient clothing options (we don't expect people to wear masks or gloves on a summer day outdoors). While the hands are continually in motion and will receive variable amounts of UV dose, the face is relatively stable. This is why measuring UV exposure on the face has advantages. For this purpose, in some embodiments the system includes a magnetic wearable system that is capable of being attached to the front of the top layer of clothing, usually a shirt. This sensor is generally always oriented in the same direction of the face, and hence will collect a UV exposure dose that correlates very closely with that of the face. Measuring on the chest also provides the advantage of having a very stable measurement, as opposed to the wrist.

The magnetic attachment system shown in FIGS. 9(a) and 9(b) comprises two magnets, one (710) disposed inside the wearable device housing and one (712) on the outside of the wearable device housing (700). The magnet in the inside of the wearable device (710) housing sits close to the bottom of the unit (740), and the wearable device is meant to be placed on top of the outer layer of clothing (750) in the upper torso region of the user (see FIG. 9(b). The other magnet is meant to be placed on the opposite side of the outer layer of clothes. In this manner, the attraction of the 2 magnets makes the device press against the fabric of the garment, providing a secure grasp.

Whereas the user can freely choose any place in the fabric of the garment to place the device, its intended area of use is in the upper torso (770), as depicted in FIG. 9(b). This method is superior to others based on specific features in clothing, such as clips, which can only be placed on edges of clothing. It is also superior to pin or brooch attachments in that it does not pierce the clothing. It is conceivable however, that in some embodiments there the wearable device can be positioned elsewhere.

This system includes similarly shaped (e.g., cylinders of same diameter, rings of same internal and external diameters, but not necessarily height) magnets (see FIG. 10), as projected to the plane that lies in between them in order to ensure that they are aligned when snapped together. The ring-shaped magnets allow for the design of a particular charging system, as described below.

4. Charging System

An exemplary charging system shown in the side and perspective views of FIGS. 11A and 11B uses conductive, concentric ring shaped conductors (810) in the bottom of the device (800), which are connected to different signals in the internal circuitry of the device. The charger makes use of spring loaded contacts (820) in a flat configuration, at varying distances from a common axis of symmetry normal to the said plane, which coincide with the radii of the conductive rings on the device, and carry the electrical signal intended to make connection with that specific ring. This is depicted in FIGS. 11A and 11B. In this way, electrical connection is ensured, irrespective of the relative rotation angle between the device and the charger around the common axis of symmetry.

The charger may optionally also include a magnet or ferromagnetic material. This will cause magnetic attraction to the magnet inside the device housing and allow for better engagement of the charger and device. The strength and position of such a magnet is also adjusted so that the magnetic clamping causes the electrical contacts on both device and charger to align correctly with each other.

5. Sensor Value Correction Using Orientation Detection

As described above, the wearable device (100) can be attached to the front of the clothing using a magnetic attachment system. The purpose of the wearable device is to measure the exposure on the face ($I_{face}$) (510), and hence needs to be aligned as flat against the chest as possible. However, depending on the material of clothing used and where the device is placed, the device may, in practice, be tilted from this ideal flat position corresponding to the face orientation (520). Further, the tilt of this device might be changing very rapidly, such as when the wearable is attached to a loose shirt while the user is running. This would cause an unstable measurement, despite the user's face receiving a uniform amount of UV exposure. Stability and accuracy are both important, in order to accurately estimate UV dose. We use sensors to detect the device orientation (530) in real-time. This knowledge is then used to correct the measured exposure ($I_{device}$) (500) to correlate to that on the face. This serves the dual purpose of correcting errors and stabilizing the measurement of UV.

Orientation detection is performed by a set of orientation sensors (e.g., orientation sensor 135, in FIG. 1) including accelerometers and gyroscopes, which are known. These determine the angular position of an object in three dimensions in terms of pitch, roll and yaw. We are primarily interested in the angular rotation of the device around the horizontal axis passing from left to right through the human face. We will call this angle the tilt ($\varphi$) (FIGS. 12A and 12B) (540). The tilt angle is an output from the orientation sensor, or derived from output from the orientation sensor, and is input to computer executable methods herein.

The actual irradiance incident normally on the face ($I_{face}$) can be then estimated by the system in terms of the tilt and the irradiance incident on the device ($I_{device}$) as:

$$I_{face} = I_{device} \cos \varphi$$

6. Real-Time Notification from Wearable Device to Mobile Device Using Geo-Fencing The wearable device (100) can be adapted to able to alert the user in certain scenarios e.g. when the daily UV exposure has exceeded safe limits, or the wearable device is running out of battery, or the wearable device is being obstructed by something. We will broadly refer to such a situation as an alert condition. The notification needs to happen soon after the alert condition is detected on the wearable device, so as to not risk the user's health, and hence needs to be in real-time. We cannot assume that the wearable device is always connected to the user's mobile device wirelessly. This is due to a number of practical reasons e.g., the user might have dismissed the mobile application on their mobile device, or the OS of the mobile device might have severed the wireless connection in order to conserve battery. Further, in most wireless protocols, the slave cannot initiate contact with the master. In this case, the slave is the wearable device, the master is the mobile device, and this is a common condition for Bluetooth/Bluetooth Low Energy. Under such circumstances, we propose a novel and unique method to notify the user of the alert condition, based on geo-fencing.

Geo-fencing is the science of alerting a mobile user when the device has entered a particular location. Normally, this location is determined using the GPS chip on the mobile device, although increasingly commonly WiFi signals are also being used to improve this location estimate. Beacon-based geo-fencing allows even more fine-grained location estimates by being able to determine if the mobile device is in the vicinity of a Bluetooth beacon whose location is known a priori. Previously, this has purely been used for more accurate location estimates, but our proposed system utilizes the same method for sending alerts from any Bluetooth-enabled device.

FIG. 13 shows an exemplary flow for user notification. The application on the mobile device (670) can be set up for beacon-based geo-fencing (675). This allows the device to be alerted whenever it is in the vicinity of a beacon with a specific identifier. This alert identifier is known to both the wearable device and the mobile device and stored in a database (660), which may exist in-memory on the wearable device and mobile device, or reside in the cloud. Three alert conditions may exist on the device: (a) the wearable device is covered by an object e.g. the user's jacket (610) (b) the measured UV dose exceeds the user's selected threshold (620), or (c) the wearable device is running low on battery (630). When the microcontroller on the wearable device (640) detects its alert condition, it switches to advertising with that same pre-specified alert identifier (650), which it looks up from the database (645). The identification information is contained in the advertisement packet of the beacon (655). The system utilizes different identifiers to indicate different alert conditions. When the mobile device is alerted of the presence of a beacon (680), it first derives the alert identifier from the beacon advertisement packet (681). It then checks its identifier against its list of known identifiers (682). If the identifier corresponds to a known alert condition, the mobile device displays this alert condition to the user (685). If the user acknowledges the alert condition, the mobile device then connects wirelessly (note that the mobile device as the master can initiate connection) and sends an acknowledgement to the wearable device (690). This acknowledgement causes the wearable to stop advertising as a beacon (691) and resume normal operation by clearing the alert condition (692).

7. Use of Diffuser with Cosine Response

In some embodiments the wearable device is adapted and configured such that the sensors lie under an opaque casing. In order for light to reach these sensors, the casing can include windows in the material to transmit light. However, depending on the angle of the incident light and the depth under the casing where the sensor lies, it is easily possible for incident light to not reach the sensor, thus giving inaccurate readings (FIG. 14(a)(i)). For this purpose, the casing should have a material that is capable of accepting light at different incident angles and removing this angular information when transmitting it to the sensor below (FIG. 14(a)(ii)). In some embodiments the wearable device thus includes one or more optical diffusers as the filling material for the aforementioned windows. Here we describe the desired response of the diffuser material.

The amount of irradiance in a flat area element A from a planar source of light (direct light from the sun can be assumed to be a planar source, since the origin of the rays is so far away that they are almost parallel) reaches a maximum when the normal of the element is parallel to the incoming rays. Let's call this maximum $I_{max}$. If the area is then tilted so that the angle between its normal and the incoming rays is θ (as seen in FIG. 14(b)), then the irradiance varies as a cosine of θ multiplied by the maximum radiation. Note that this is independent of rotation of the said area element around its normal.

Irradiance of a tilted plane can be expressed then as a function of θ such that:

$$I(\theta) = I_{max} \cos(\theta) \quad \text{(Eq. 7.1)}$$

In order to be true to the physical quantity being measured, the wearable device should exhibit the same angular response when the sensor is tilted with respect to the sun. The optical diffuser, placed on top of the UV and optical sensors, needs to have the properties of a perfect Lambertian diffuser, which will allow the recovery of the desired cosine angular response (Eq. 7.1). The device includes windows of a specific material aimed at resembling as close as possible a Lambertian transmission diffuser. The diffuser material may be cut into window-shaped pieces and adhered underneath the openings to allow the light in, or may be assembled as a single piece directly underneath the windows using clips in the casing, as depicted in FIG. 15. In this depiction, the top case (1050) comprises clips (1030) into which the single-piece diffuser (1040) is able to snap in place, and be held firmly. The plurality of windows in the top case are directly positioned above the sensors of interest (1010, 1020), which reside on the printed circuit board (PCB) (1000).

8. Covering Detection and Alert

As previously described, in some embodiments the wearable device is magnetically attached to the front of the clothing. It is possible that the user mistakenly covers this device, such as when wearing a jacket over the shirt. This would cause the covering to block all UV to the device, and thus render it unable to estimate the radiation incident on the face. In order to overcome this problem, in some embodiments the wearable device includes a covering detection system, which is capable of alerting the user, so that the covering may be promptly removed.

In this embodiment, in order to detect covering, a proximity sensor (e.g., proximity sensor 130 in FIG. 1) is used, which includes an infra-red (IR) LED (1100) and an IR detector (1110). The IR LED sends pulses outward (1130). The two components are place under a window of the top case (1150), which is covered by diffuser material (1120). Without any covering items, the IR pulses escape and are not captured by the IR detector (see FIG. 16A). If any object is covering the wearable (1140), there is significantly high reflection of IR from it and is picked up as a signal in the IR detector, as shown in FIG. 16B.

The flow for proximity detection is shown in FIG. 17. The micro-controller (1170) pulses the IR LED (1171) and polls the value of the IR detector (1172) in sequence. If the IR detector signal (PROX) is found to exceed a certain proximity threshold ($PROX_{th}$) (1174), then the microcontroller increments a counter (1176), else clears the counter (1178). When the counter ($Counter_{PROX}$) exceeds a pre-specified threshold (1180), the microcontroller determines that there is material covering the wearable device. It then triggers an alert condition (1182), which in turn will notify the user that their device is covered by something.

9. Night Detection for Sleep Mode

The wearable device needs to not only be accurate, but also power-efficient so that it is able to maximize the amount of UV data captured on a single charge. For this purpose, collecting UV data in the absence of the sun i.e. before dawn or after dusk, is an unnecessary drain on the power supply. Being able to sleep during this time saves both battery and memory for collecting data. However, it is not expected that the wearable device will be constantly connected to the mobile device, which would make it unaware of sunrise and sunset times. In order to overcome this issue, we utilize an algorithm based on the existing sensors, which determines when to sleep and when to wake up the device.

FIG. 18 shows an exemplary sleep mode algorithm in more detail. In the designed system, there are two modes—sleep mode (900) and active mode (910). In active mode all sensors are active and the microcontroller polls these sensors to aggregate the UV data. From polling the visible light sensor (950) it determines if the reading (VIS) is above a certain threshold. It also polls the proximity sensor (PROX) to ensure that there is nothing covering the device. If the reading is found to be below a pre-determined light/dark threshold ($VIS_{light/dark}$) (940), and the proximity reading exceeds the covered threshold (945), a counter is incremented (930), else the counter is cleared (935). If the counter exceeds a pre-specified value ($Counts_{dark}$) (920), indicating the condition of darkness has persisted for some time, the device is put into sleep mode (900). Running a counter-based scheme helps prevent against noisy readings, or sudden darkness conditions e.g., when a train passes through a tunnel. If the proximity sensor senses something is covering the device rather than darkness due to the absence of sun, the system can send an alert to the user, as described above.

In sleep mode all sensors apart from the visible light sensor are shut down. The visible light sensor is also polled (950) at a much reduced interval by the micro-controller in order to conserve more energy. If the visible light reading is found to cross the same light/dark threshold ($VIS_{light/dark}$) (940), then the microcontroller puts the device back into active mode.

10. User-Selectable Safe Thresholds Based on UV Exposure History

In order to avoid harmful effects of UV over-exposure (exposure over a prolonged period of time) such as sunburn or phototoxicity, it is important to understand and determine safe thresholds for UV dose (Sayre, R. & Desrochers, D. "Skin type, minimal erythema dose (MED), and sunlight acclimatization". *Am. Acad. dermatology* 439-443 (1981); Heckman, C. J. et al. "Minimal Erythema Dose (MED) testing". *J Vis. Exp.* e50175 (2013). doi:10.3791/50175). We have already described a system for alerting the user when such safe thresholds are exceeded. Here we describe a method for selecting such a threshold based on past exposure history, along with disease activity. We define the term disease activity to indicate symptom occurrences and general well-being of the user, as tracked on a periodic basis via the mobile application. Symptoms include skin reactions (e.g., erythema, sunburn, etc.) and systemic symptoms (e.g. joint pain, etc.). Our system asks the user to rate their disease activity daily on a scale of 0 (no symptoms, good health), to 10 (lots of symptoms, poor health). Note that the threshold may apply to a full day's UV dose, or to some other time unit, such as a week, or an hour. The unit of time may also be user-selectable, e.g., a user may choose to select a threshold for hourly UV dose, and a different threshold for daily UV dose. We will describe the rest of this section using daily threshold as an example, but it easily extends to other time periods. Also, we will describe the example using UV dose, but it is equally applicable to UVA dose or UVB dose individually. By looking at both disease activity and UV dose, the user decides to manage a dose of UV exposure that he or she thinks may be safe for his or her own wellbeing. Different users have different tolerances to UV and our method enables anybody to manage the right amount of UV dose.

The threshold selection occurs on the mobile device, where all or some of the following information can be presented to the user:

(i) Minimum daily UV dose (over period of usage of the device)

(ii) Maximum daily UV dose (over period of usage of the device)

(iii) Average daily UV dose (iv) Symptoms by date (v) UV dose history by date

FIGS. 19A and 19B show one depiction of this information. The top graphs labeled "UV daily exposure" represents UV dose in units of Joules/m$^2$ (B. L. Diffey et al., "The standard erythema dose: a new photobiological concept", *Journal of Photodermatology, photoimmunology & photomedicine*, Vol. 13, 1997). This is visually presented on top of another graph with a representation of disease activity information, and can either be on the same graph, or on an adjacent (the information can be presented in many different ways). The disease activity is, in this embodiment, shown as a score, which was recorded by the user on a daily basis. The daily minimum, maximum and average dose can also be shown on the plot. The maximum of the UV dose on the Y-axis is set according to the maximum daily UV dose ever received by the user. By understanding the time history of the symptoms, the user is then able to select a daily threshold using a slider (or some other form of input), which lies between zero and the maximum UV dose the user has ever been exposed to. The threshold can be selected so that future symptoms can be avoided or minimized. For example, if a relatively high UV dose is associated with certain diseases symptoms, as indicated on the screen, a user can select a threshold dose that is below the level of the dose that was associated with the disease symptoms. Such thresholds can also be determined for UVA and UVB separately. Such a threshold can be determined for hourly, daily, weekly, monthly doses. Threshold can be chosen over any number of hours, days, weeks, months, and in some embodiments the user can select the time epoch for which to set this threshold. In some embodiments the time histories are broken up into epochs of time, and can be the same epochs, or they can be broken up into different epochs of time.

One embodiment of the user interaction flow for setting the threshold is shown in FIG. 20. The process is started with the user requesting to set their UV threshold (1200). This action may be in the form of tapping a button on the mobile application (1290) (e.g., FIG. 19A), or may use other forms of input such as voice. When the mobile application receives this request, it fetches the user's UV exposure history (1210) from the UV exposure history database (1215), and the user's current UV threshold from its respective database (1245). The database may reside on the mobile device running the application, or in the cloud, in which case the data would be retrieved over the internet. Concurrently, the user's disease activity information is also retrieved (1220) from the disease activity database (1225). These two pieces of data are used to draw two bar graphs to display the information simultaneously (1230). It is important to view both pieces of data at the same time, since a safe threshold may only be inferred from how UV dose affected disease activity in the past. The line corresponding to the current UV threshold is drawn across the UV dose graph (1240), which is shown in FIG. 19A via the horizontal line in the top graph, and the user is a given a visual cue of which days they exceeded their threshold by coloring bars above the threshold differently (1250) (as can be seen in the different highlighted areas above the line in the top graph in FIG.

19A, for an example). When the user moves the threshold by dragging the threshold line up or down (see FIG. 19B), the threshold line is re-drawn at the new threshold value (1245). If the user confirms their new threshold by tapping on a confirmation button (1295) (shown in FIG. 19B), this new threshold is saved in the UV threshold database (1245). This is an example of how a user can select a threshold, and also optionally change a threshold after it has already been set. This ability to control the threshold based on symptoms personalizes the threshold for each patient, providing much better care for the patient.

11. Accurate Estimation of Safe Amount of Time to Spend in Current Conditions

While the wearable device measures the aggregated UV dose, it is difficult for users to have a notion of how fast they are approaching safe limits of UV dose (which may be user-selected, as described herein). Thus, it is important that the system provide an estimate of how much time can be safely spent outside current weather conditions. The mobile device can provide this information, after the current UV dose has been wirelessly obtained from the wearable device. This time estimate needs to be accurate, because overestimating the time can have serious health consequences for the user, while underestimating the time deprives the user of valuable healthy UV.

We assume that the current UV dose ($D_{current}$) and current UV exposure ($I_{current}$) have been obtained from the wearable device, and a safe threshold ($D_{safe}$) for the UV dose is known, or has been pre-set by the user. Note that both the current and safe dose may be related purely to UVA, or UVB, or the combination of the two. The time to reach the dose limit ($T_{safe}$) can be estimated by solving the following equation:

$$D_{current} + \int_{t=0}^{T_{safe}} I(t)dt = D_{safe} \quad (Eq. 11.1)$$

I(t) represents the UV exposure as a function of time. For accurate prediction of $T_{safe}$, we need to have an accurate estimate for this.

UV exposure varies with the solar zenith angle (U.S. Pat. No. 9,068,887) ($\varphi$), which in turn is a function of time (t) as well as the location. FIG. 21 shows the variation of UV index over a typical day. We fit a sinusoidal function to approximate this curve, which is also shown in the figure. This allows us to approximate the UV exposure as:

$$I(t) = I_{max} \sin\frac{\pi(t - T_{sunrise})}{(T_{sunset} - T_{sunrise})}, \text{ if } T_{sunrise} < t < T_{sunset} \quad (Eq. 11.2)$$
$$= 0, \text{ otherwise}$$

where $T_{sunrise}$ and $T_{sunset}$ represent the times of sunrise and sunset respectively. The information for these times is readily available for a given location from internet APIs. The mobile device has access to both such internet APIs and the location of the device. The maximum UV exposure is estimated from the current UV exposure ($I_{current}$) by solving for the above equation at the current time ($t_{current}$).

$$I_{max} = \frac{I_{current}}{\sin\frac{\pi(t - T_{sunrise})}{(T_{sunset} - T_{sunrise})}} \quad (Eq. 11.3)$$

By using this form of the function I(t) in Eq. 11.1, it is now possible to analytically solve for the safe amount of time ($T_{safe}$) that can be spent in current conditions. This estimate can be updated continuously as new readings for UV exposure are received from the wearable device. In order to guard against sudden fluctuations in UV, e.g., when a cloud goes over the sun, we also form an estimate for the current UV exposure based on a weighted average of previous samples (Eq. 11.4).

$$I_{current}(t_0) = a_0 I_{current}(t_0) a_1 I_{current}(t_0-T) + a_2 I_{current}(t_0-2T) + \ldots + a_n I_{current}(t_0-nT) \quad (Eq. 11.4)$$

Once this is calculated, this can be displayed on the mobile device to the user, to inform them of the amount of time that is safe to be spent in the current environmental conditions. If the user is detected to be indoors (e.g., using any of the environmental detection algorithms herein), then the time display can be dismissed and the mobile device can instead inform the user that they are safe from UV radiation.

An exemplary computer executable method for estimating the safe amount of time to spend in current UV conditions is shown in FIG. 22. The wearable device sends the values of current exposure (1300) and current dose (1310) using its wireless connection to the mobile device. The mobile device maintains a first-in-first-out (FIFO) queue (1320) to cache the past few values of UV exposure. From these values an average current exposure can be estimated (Eq. 11.4). The mobile device also looks up the user's pre-selected UV threshold from a database (1350) which might exist on the device or in the cloud. It also utilizes its internet connection to get sunrise and sunset times from a weather API (1360). With these pieces of information (1325, 1355, 1315, 1365), the mobile device computes the safe amount of time for the user to spend in current conditions (1330), by numerically solving Eq. 11.1. This information is then displayed to the user (1340) using the mobile device's visual interface.

Any of the computer executable methods herein may be performed on a wearable device (which in fact need not be worn, but could simply be placed next to a subject, such as on desk) or on a mobile device, or some parts of the computer executable methods may be performed on a wearable device while some parts are performed on a mobile device. The specific examples herein are illustrative.

Additional concepts:

1. A wearable UV sensing device comprising a UVA sensor and a UVI sensor.

2. The device of concept 1 wherein at least one of the sensors comprises a UV diode and a filter.

3. The device of concept 2 wherein the spectral response of the UV diode and filter combine to mimic the erythemal weighting function.

4. The device of concept 1 wherein the sensors have the same response.

5. The device of concept 1 wherein the sensors have different responses.

6. A wearable UV sensing device comprising a UVA sensor, a UVI sensor, and a visible light sensor.

7. A wearable UV sensing device comprising:
a wearable sensing housing comprising a first magnetic element, and a second magnetic element disposed outside the housing.

8. The device of concept 7, wherein the second magnetic element is not physically attached to the housing.

9. The device of concept 7 wherein the second magnetic element is physically attached to the housing.

10. The device of concept 7 wherein the first and second magnetic elements have substantially the same shape.

11. The device of concept 10 wherein the first and second magnetic elements do not have the same dimensions.

12. The device of concept 7 wherein the first magnetic housing is disposed within the housing.

13. The device of concept 12 wherein the first magnetic element is disposed in a plane that is parallel with a bottom surface of the housing.

14. The device of concept 13 wherein the first magnetic element is closer to the bottom surface than a top surface of the housing.

15. A charging system for a wearable UV sensing device comprising:
a wearable housing comprising a central conductor and at least one annular conductor around the central conductor, the conductors disposed at an external surface of the housing;
a charger including at least first and second conductive contacts, the first and second contacts spaced from each other in the charger and the central conductor and annular conductor spaced from each other such that the first and second contacts are in contact with the central conductor and the annular conductor, respectively, when the housing and charger are engaged.

16. The charging system of concept 15 wherein the charger further comprises a first magnetic element that is magnetically attracted to a second magnetic element disposed within the wearable housing.

17. The charging system of concept 16 first and second magnetic elements are positioned and configured such that their magnetic attraction facilitates the alignment of the contacts and the conductors.

18. The charging system of concept 16 wherein the first and second magnetic elements are substantially the same size.

19. A personal UV sensing system, comprising
a wearable UV sensing device comprising an orientation sensor, and a remote device; and
a computer implemented method that estimates irradiance on a face of an individual utilizing irradiance incident on the wearable UV sensing device and an angle of tilt of the wearable UV sensing device relative to a horizontal plane passing through a human face.

20. A system including a wearable device adapted to send an alert to a remote device, comprising:
a wearable device adapted to, upon detection of an event, advertise as a beacon with an identifier associated with the event;
a remote device adapted to detect the beacon, compare the identifier associated with the beacon with a set of known identifiers, and create a user alert to the occurrence of the event.

21. The system of concept 20 wherein the remote device is further adapted to, upon a user acknowledgement of the alert, establish a wireless connection with the wearable device and communicate an acknowledgement to the wearable device.

22. The system of concept 21 wherein the wearable device is further adapted to, upon receipt of the acknowledgement, stop advertising as a beacon.

23. The system of concept 20 wherein the event is at least one of: a UV exposure has reached a threshold amount, the wearable device is low on power, and a sensor in the wearable device is obstructed.

24. A wearable UV sensing device, comprising:
a housing with an aperture therein and an optical diffuser disposed in the aperture.

25. The device of concept 24 further comprising a UV sensor secured within the housing and disposed below the optical diffuser.

26. The sensing device of concept 24 wherein the optical diffuser is a Lambertian, or substantially Lambertian, optical diffuser.

27. A wearable UV sensing device comprising a UV sensor and a proximity sensor.

28. The device of concept 27 wherein the proximity sensor comprises a light source and a light detector.

29. The device of concept 28 wherein the light source comprises an infra-red LED and the light detector comprises an infra-red detector.

30. The device of concept 28 wherein the sensing device further comprises a controller that is adapted to pulse the light source and polls a value of the light detector in sequence.

31. The device of concept 30 wherein the controller is adapted to compare the value polled with a threshold to determine if the proximity sensor is covered.

32. The device of concept 31 further comprising a remote device adapted to create an alert that the proximity sensor is covered.

33. The device of concept 27 wherein the UV sensor includes one or more of a UVA sensor, a UVI sensor, and UVB sensor.

34. A device of any of concept 27-33 wherein the device further comprises a visible light sensor.

35. A UV sensing system, comprising:
a remote device with a user interface, the user interface displaying at least one aspect of UV exposure history, the user interface further including a user input selector adapted to allow a user to select a UV threshold based on the at least one aspect of UV exposure history.

36. The system of concept 35 wherein the user interface is adapted to allow a user to select a UV threshold based on a threshold continuum.

37. The system of concept 35 wherein the at least one aspect of UV exposure history includes UV dose exposure.

38. The system of concept 35 wherein the user input selector is at least one of a text field, a slider, a selectable menu.

39. The system of concept 35 wherein the at least one aspect of UV exposure history includes a minimum and maximum exposure, and the user input selector allows the user to select a UV threshold between the minimum and maximum UV exposure.

40. The system of concept 35 wherein the user interface further displays patient symptoms as they are related to at least aspect of the exposure history.

41. A personal UV sensing device, comprising
a sensor housing and at least one UV sensor inside the housing, and at least one reflection reducing element adapted to reduce reflection of light therefrom.

42. The device of concept 41 wherein the reflection reducing element is made of a reflection reducing material.

43. The device of concept 41 wherein the reflection reducing element is coated with a reflection reducing material.

44. The device of concept 41 wherein the reflection reducing element is disposed within the housing such that it isolates the light path of the UV sensor.

45. The device of concept 41 wherein the reflection reducing element is disposed within the housing between the UV sensor and adjacent components.

46. The device of concept 41 wherein the reflection reducing element is part of the housing.

47. The device of concept 41 wherein the reflection reducing element has a non-linear configuration that contributes to its adaptation to reduce reflection.

48. The device of concept 41 wherein the reflection reducing element has a height greater than a width.

49. The device of concept 41 comprising first and second reflection reducing elements, each one disposed on a side of the UV sensor.

50. A wearable UV sensing device with a sleep mode, comprising:
a UV sensor;
a visible light sensor;
a computer implemented method that is adapted to use a signal indicative of an output of the visible light sensor to determine if a condition of darkness has persisted, and to initiate a sleep mode of the device.

51. The device of concept 50 wherein the computer implemented method is adapted to deactivate or reduce the use of the UV sensor in sleep mode.

52. The device of concept 50 wherein in the sleep mode the visible light sensor remains activated to some extent.

53. The device of concept 50 wherein the computer implemented method includes a counter that is incremented when the signal indicative of an output of the visible light sensor is above a certain threshold, and when the counter reaches a threshold value, initiates the sleep mode.

54. The device of concept 50 wherein the computer implemented method is adapted to poll the visible light sensor in sleep mode and to determine if a condition of lightness has persisted, and if so, initiate an active mode of the device in which the UV sensor is activated.

55. The device of concept 50 wherein the computer implemented method is adapted to poll the visible light sensor in sleep mode at a reduced rate compared with an active mode of the device.

56. A personal UV sensing system, comprising
a wearable sensing device and a remote device,
a computer implemented method that receives as input a signal that is indicative of an output from a UVI diode on the wearable sensing device, and compares the input to a threshold UV characteristic to make a determination if the UVI diode is outdoor or indoors.

57. A personal UV sensing system, comprising
a wearable sensing device and a remote device,
a computer implemented method that receives as input a signal that is indicative of an output from a UVA diode on the wearable sensing device, and compares the input to a threshold UVA characteristic to make a determination that the UVA diode is near a window indoors or away from a window indoors.

58. A personal UV sensing system, comprising
a wearable sensing device and a remote device,
a computer implemented method that receives as input a signal that is indicative of an output from a visible light sensor on the wearable sensing device, and compares the input to a threshold visible light characteristic to make a determination that the light sensor is in the shade or not in the shade.

59. A personal UV sensing system, comprising
a computer implemented method that receives as input a signal that is indicative of an output from a visible light sensor on the wearable sensing device and a signal that is indicative of an output from a UVI diode on the wearable sensing device, and utilizes the signals to make a determination if the visible light sensor and the UVI diode are in a cloudy environment or in a sunny environment.

60. Any of the systems of concept 56-59, wherein the system is further configured to select a particular model for UV Index prediction based on the determination made by the computer implemented method.

61. A personal UV sensing system, comprising
a wearable sensing device and a remote device; and
a computer implemented method that is adapted to use a signal that is indicative of an output from a UV sensor on the wearable sensing device and a solar zenith angle of the remote device to estimate amounts of UVA and UVB received by the UV sensor.

62. The system of concept 61 wherein the computer implemented method is adapted to calculate a quantitative relationship between UVB and UVA using the solar zenith angle of the remote device.

63. The system of concept 61 wherein the computer implemented method is adapted to calculate a ratio of UVB to UVA using the solar zenith angle of the remote device.

64. The system of concept 63 wherein the computer implemented method is adapted to estimate the amounts of UVA and UVB using the signal that is indicative of an output from a UV sensor and the ratio of UVB to UVA.

65. The system of concept 61 wherein the computer implemented method is disposed in the remote device.

66. A personal UV sensor system, comprising:
a wearable device and a remote device,
the system adapted to estimate an amount of time that can be spent in the current weather conditions before reaching a threshold UV dose level by forecasting a change in UV over time, the system further adapted to display the amount of time on the remote device.

What is claimed is:
1. A wearable UV sensing device comprising:
a wearable housing that comprises a UV sensor, a visible light sensor, a proximity sensor, and a storage device that has stored thereon a computer executable method for automatically causing the wearable UV sensing device to enter a sleep mode, the computer executable method comprising:
receiving information indicative of a signal from the visible light sensor;
using the information to determine if a condition of darkness adjacent the UV sensor exists;
receiving information indicative of a signal from the proximity sensor and determining if a material covering the device is responsible for the condition of darkness; and
initiating the sleep mode if a determination has been made that a condition of darkness exists and it is not caused by a material covering the proximity sensor.

2. The method of claim 1 wherein using the information to determine if a condition of darkness adjacent the UV sensor exists comprises:
comparing the information with a visible light threshold;
incrementing a counter if the information is not above the visible light threshold; and
comparing counts from the counter with a threshold count,
wherein the initiating step comprises initiating a sleep mode if the counts are greater than the threshold count.

3. The method of claim 1, further comprising maintaining an active mode of the UV sensing device if a determination has been made that a condition of darkness adjacent the UV sensor does not exist.

4. The method of claim 1, further comprising, after initiating sleep mode, initiating an active mode in which a UV sensor is activated based on the information indicative of a signal from the visible light sensor if the information is greater than a visible light threshold.

5. The method of claim 1 wherein initiating a sleep mode comprises decreasing the use of the UV sensor.

6. The method of claim 1 wherein initiating a sleep mode comprises maintaining a use of the visible light sensor.

* * * * *

UNITED STATES PATENT AND TRADEMARK OFFICE
CERTIFICATE OF CORRECTION

PATENT NO. : 9,880,052 B2
APPLICATION NO. : 15/247837
DATED : January 30, 2018
INVENTOR(S) : Emmanuel Dumont, Shayak Banerjee and Mauricio Contreras Page 1 of 1

It is certified that error appears in the above-identified patent and that said Letters Patent is hereby corrected as shown below:

In the Claims

Column 26, Line 43, Claim 2, after "The" and before "of" delete "method" and insert --device--;

Column 26, Line 53, Claim 3, after "The" and before "of" delete "method" and insert --device--;

Column 26, Line 53, Claim 3, after "claim 1," and before "further" insert --wherein the computer executable method--;

Column 26, Line 53, Claim 3, after "further" and before "maintaining" delete "comprising" and insert --comprises--;

Column 26, Line 57, Claim 4, after "The" and before "of" delete "method" and insert --device--;

Column 26, Line 57, Claim 4, after "claim 1," and before "further" insert --wherein the computer executable method--;

Column 26, Line 57, Claim 4, after "further" and before "after" delete "comprising," and insert --comprises,--;

Column 26, Line 58, Claim 4, after "initiating" and before "sleep" insert --the--;

Column 26, Line 58, Claim 4, after "which" delete "a" and insert --the--;

Column 26, Line 62, Claim 5, after "The" and before "of" delete "method" and insert --device--;

Column 26, Line 64, Claim 6, after "The" and before "of" delete "method" and insert --device--.

Signed and Sealed this
Seventh Day of August, 2018

Andrei Iancu
*Director of the United States Patent and Trademark Office*